(12) United States Patent
Levendowski et al.

(10) Patent No.: US 8,355,769 B2
(45) Date of Patent: Jan. 15, 2013

(54) SYSTEM FOR THE ASSESSMENT OF SLEEP QUALITY IN ADULTS AND CHILDREN

(75) Inventors: Daniel J. Levendowski, Carlsbad, CA (US); Philip R. Westbrook, Fallbrook, CA (US); Chris Berka, Carlsbad, CA (US); Djordje Popovic, Oceanside, CA (US); Timothy Zavora, Reno, NV (US); Gene Davis, Oceanside, CA (US); Mirko Mitrovic, Carlsbad, CA (US); Bratislav Veljkovic, Carlsbad, CA (US)

(73) Assignee: Advanced Brain Monitoring, Inc., Carlesbad, CA (US)

( * ) Notice: Subject to any disclaimer, the term of this patent is extended or adjusted under 35 U.S.C. 154(b) by 28 days.

(21) Appl. No.: 12/726,084

(22) Filed: Mar. 17, 2010

(65) Prior Publication Data

US 2010/0240982 A1 Sep. 23, 2010

Related U.S. Application Data

(60) Provisional application No. 61/160,924, filed on Mar. 17, 2009, provisional application No. 61/184,628, filed on Jun. 5, 2009, provisional application No. 61/266,437, filed on Dec. 3, 2009.

(51) Int. Cl.
*A61B 5/0478* (2006.01)
*A61B 5/0492* (2006.01)
*A61B 5/0496* (2006.01)
*A61B 5/087* (2006.01)

(52) U.S. Cl. ........ 600/383; 600/390; 600/391; 600/393; 600/538; 600/544; 600/546

(58) Field of Classification Search ............... 600/301, 600/383, 393, 544, 546
See application file for complete search history.

(56) References Cited

U.S. PATENT DOCUMENTS

| 5,081,447 A | 1/1992 | Echols |
| 5,381,801 A | 1/1995 | McShane |
| 5,447,161 A | 9/1995 | Blazek et al. |
| 5,479,934 A * | 1/1996 | Imran ..................... 600/544 |

(Continued)

OTHER PUBLICATIONS

A Report by the American Society of Anesthesiologists Task Force on Perioperative Management of Patients with Obstructive Sleep Apnea, Practice Guidelines for the Perioperative Management of Patients with Obstructive Sleep Apnea. Anesthesiology, 2006. 104(5): p. 1081-1093.

(Continued)

*Primary Examiner* — Lee S Cohen
(74) *Attorney, Agent, or Firm* — Procopio, Cory, Hargreaves & Savitch LLP

(57) ABSTRACT

Systems and methods for assessment of sleep quality in adults and children are provided. These techniques include an apparatus worn above the forehead containing the circuitry for collecting and storing physiological signals. The apparatus integrates with a sensor strip and a nasal mask to obtain the physiological signals for the user. The form factor of this apparatus is comfortable, easy to self-apply, and results in less data artifacts than conventional techniques for capturing physiological data for analyzing sleep quality. Neuro-respiratory signals are analyzed using means to extract more accurate definitions of the frequency and severity of sleep discontinuity, sleep disordered breathing and patterns of sleep architecture. Biological biomarkers and questionnaire responses can also be compared to a database of healthy and chronically diseased patients to provide a more accurate differential diagnosis and to help determine the appropriate disease management recommendations.

32 Claims, 13 Drawing Sheets

U.S. PATENT DOCUMENTS

| | | | |
|---|---|---|---|
| 6,600,949 | B1 | 7/2003 | Turcott |
| 6,641,571 | B2 | 11/2003 | Redmond et al. |
| 6,811,538 | B2 | 11/2004 | Westbrook et al. |
| 6,970,792 | B1 | 11/2005 | Diab |
| 7,081,095 | B2 | 7/2006 | Lynn |
| 7,117,028 | B2 | 10/2006 | Bardy |
| 7,118,534 | B2 | 10/2006 | Ward et al. |
| 7,311,666 | B2 | 12/2007 | Stupp et al. |
| 7,691,067 | B2 | 4/2010 | Westbrook |
| 7,717,848 | B2 | 5/2010 | Heruth et al. |
| 2002/0165462 | A1 | 11/2002 | Westbrook et al. |
| 2002/0184050 | A1 | 12/2002 | Papageorge |
| 2002/0188205 | A1 | 12/2002 | Mills |
| 2004/0015337 | A1 | 1/2004 | Thomas et al. |
| 2004/0163648 | A1* | 8/2004 | Burton ............... 128/204.21 |
| 2005/0131288 | A1* | 6/2005 | Turner et al. ............... 600/391 |
| 2005/0234313 | A1 | 10/2005 | Rowlandson et al. |
| 2006/0100538 | A1 | 5/2006 | Genger et al. |
| 2007/0208269 | A1 | 9/2007 | Mumford et al. |
| 2007/0214013 | A1 | 9/2007 | Silverman |
| 2007/0282177 | A1 | 12/2007 | Pilz |
| 2008/0319277 | A1 | 12/2008 | Bradley |
| 2009/0240119 | A1* | 9/2009 | Schwaibold et al. ......... 600/301 |
| 2011/0098593 | A1* | 4/2011 | Low et al. ............... 600/544 |

OTHER PUBLICATIONS

Alemohammad, M., Z Khan, M Sanatkar, S Mirkhani, Ghorbandaie-Poure I., Pressure measurements during cardiac surgery—internal jugular vs. central venous. Middle East J Anestesiol, 2005; 18(2):357-65.

Argod J, Pepin J, Smith R, Levy P. Comparison of Esophageal Pressure with Pulse Transit Time as a measure of respiratory effort for scoring obstructive nonapneic respiratory events. Am J Respir Crit Care Med vol. 162 (2000) 87-93.

Aurell, J. and D. Elmqvist, Sleep in the surgical intensive care unit: continuous polygraphic recording of sleep in nine patients receiving postoperative care. Sr Med J (Clin Res Ed), 1985. 290(6474): p. 1029-1032.

Benumof, J.L., Obstructive sleep apnea in the adult obese patient: implications for airway management, Anesthesiology Clinics of North America, 2002. 20(4): p. 789-811.

Benumof, J.L., Obesity, sleep apnea, the airway, and anesthesia. Current Opinion in Anaesthesiology, 2004. 17(1 ): p. 21-30.

Brown, K,: Intermittent Hypoxia and the Practice of Anesthesia. Anesthesiology. 2009 110(4). p. 922-927.

Cannesson M, Besnard C, Durand PG, Bohe J, Jacques D. Relation between respirator variations in pulse oximetry plethysmographic waveform amplitude and arterial pulse pressure in ventilated patients. Crit Care. Oct. 5, 2005;9(5):R562-8. Epub Aug. 23, 2005.

Catley, DM., et al., Pronounced, episodic oxygen desaturation in the postoperative period: its association with ventilatory pattern and analgesic regimen. Anesthesiology, 1985, 63(1): p. 20-28.

Chung et al., A Systemic Review of Obstructive Sleep Apnea and Its Implications for Anesthesiologists, Ambulatory Anesthesiology, vol. 107, No. 5, Nov. 2008, pp. 1543-1563.

Cox P, Johnson JO, Tobias JD. Measurement of central venous pressure from a peripheral intravenous catheter in the lower extremity. South Med J. Jul. 2005;98(7):698-702.

Cronin, A., et al., Opioid inhibition of rapid eye movement sleep by a specific mu receptor agonist, Br J Anaesth. 1995. 74(2): p. 188-192.

Den Herder, Cindy et al., Risks of General Anaesthesia in People with Obstructive Sleep Apnoea, BMJ, vol. 329, Oct. 23, 2004, pp, 955-959 and 1 cover sheet.

Deutscher, R., et al., OSA protocol promotes safer care. Anesthesia Patient Safety Foundation Newsletter 2002-2003: p. 56-60.

Ellis, B.W. and H.A. Dudley, Some aspects of sleep research in surgical stress. J Psychosom Res, 1976. 20(4): p. 303-308.

Farre R, Montserrat JM, Navajas D. Noninvasive monitoring of respiratory mechanics during sleep. Eur Respir J. Dec. 2004;24(6):1052-1060.

Finkel, K., et al., Obstructive Sleep Apnea: The Silent Pandemic. In ASA Annual Meeting. 2006, Chicago, IL.: 1 page.

Finkel, K, et al., The Silent Perioperative Pandemic. Sleep Review, 2006. 7(4): p. 56-60.

Foo J, Wilson S, Bradley A, Williams G. Harris M, Cooper D. Use of pulse transit time to distinguish respiratory events from tidal breathing in sleeping children. Chest 2005; 128; 3013-3019.

Foo JY, Wilson SJ. Estimation of breathing interval from the photoplethysmographic signals in children. Physiol Meas. Dec. 2005;26(6):1049-1058. Epub Oct. 31, 2005.

Gali, B.: Identification of Patients at Risk for Postoperative Respiratory Complications Using a Preoperative Obstructive Sleep Apnea Screening Tool and Postanesthesia Care Assessent. Anesthesiology 2009 110(4). p. 869-877.

Gali, Bhargavi et al., Management Plan to Reduce Risks in Perioperative Care of Patients with Presumed Obstructive Sleep Apnea Syndrome, JCSM Journal of Clinical Sleep Medicine, vol. 3, No. 6, 2007, pp. 582-588.

Gentil, B., et al., Enhancement of postoperative desaturation in heavy snorers. Anesth Analg, 1995. 81 (2): p. 389-392.

Gisolf J, Van Lieshout J, Van Heusden K, Pott F, Stok W, Karemaker J. Human cerebral venous outflow pathway depends on posture and central venous pressure. J Physiol 560.1 (2004) 317-327.

Gupta, R., et al., Postoperative complications in patients with obstructive sleep apnea syndrome undergoing hip or knee replacement: a case-control study. Mayo Clinic Proceedings, 2001. 76: p. 897-905.

Haba-Rubio J, Darbellay G. Herrmann FR, Frey JG, Fernandes A, Vesin JM, Thiran JP, Tschopp JM. Obstructive sleep apnea syndrome: effect of respiratory events and arousal on pulse wave amplitude measured by photoplethysmography in NREM sleep. Sleep Breath (2005) 9: 73-81.

International Search Report and Written Opinion for PCT/US2010/027679 issued Oct. 19, 2010, 11 pages.

International Search Report/Written Opinion issued in PCTUS2007071242 on Mar. 13, 2008, 11 pages.

Johansson A, Oberg PA. Estimation of respiratory volumes from the photopiethysmographic signal. Part 1: Experimental results, Med Biol Eng Comput. Jan. 1999;37(1):42-7.

Johansson A, Oberg PA. Estimation of repiratory volumes from the photoplethysmographic signal. Part 2: A model study. Med Biol Eng Comput. Jan. 1999;37(1):48-53.

Johansson A, Strornberg T. Influence of tidal volume and thoracoabdominal separation on the respiratory induced variation of the photoplethysmogram. J Clin Monit Comput 2000;16(8):575-81.

Johansson A. Neural network for photoplethysmographic respiratory rate monitoring. Med Biol Eng Comput. May 2003;41(3):242-8.

Kaw, R., et al., Unrecognized Sleep Apnea in the Surgical Patient: Implications for the Perioperative Setting. Chest, 2006. 129(1): p. 198-205.

Keifer, J., et al., Sleep Disruption and Increased Apneas after Pontine Microinjection of Morphine. Anesthesiology, 1992. 77(5): p. 973-982.

Kheterpal, Sachin et al., Prediction and Outcomes of impossible Mask Ventilation, Anesthesiology, vol. 110, No, 4, Apr. 2009, pp. 891-897.

Knill, R., et al., Anesthesia with Abdominal Surgery Leads to intense REM Sleep during the First Postoperative Week, Anesthesiology, 1990. 73(1): p. 52-61.

Kushida C, Giocomini A, Lee M, Guilleminault C, Dement W. Technical protocol for the use of esophageal manometry in the diagnosis of sleep-related breathing disorders. Sleep Med 3(2002) 163-173.

Leonard P, Grubb NR, Addison PS, Clifton D, Watson JN. An algorithm for the detection of individual breaths from the pulse oximeter waveform, J Clin Monit Comput. Dec. 2004;18(5-6):309-312.

Lickteig, Carla et al., Risks of OSA and Anesthesia, Sleep Review, Jan./Feb. 2003, 5 pages.

Loadsman, J. and D. Hillivian, Anaesthesia and sleep apnoea. British Journal of Anaesthesia, 2001, 86(2): p. 254-266.

Lofsky, Ann. Sleep apnea and narcotic postoperative pain medication: a morbidity and mortality risk. Anesthesia Patient Safety Foundation Newsletter, Summer 2002: 24-25.

Magder S. How to use central venous pressure measurements. Curr Opin Crit Care. Jun. 2005;11(3):264-70.

Mannheimer P, O'Neil M, Konecny E. The influence of large subcutaneous blood vessels on pulse oximetry. J Clin Monitor Comput 18:179-188, 2004.

Nakajima K, Tamura T, Milke H. Monitoring the heart and respiratory rates by photoplethysmography using a digital filtering technique. Med Enq Phys 1996 1 8(5) 365-372.

Neligan, Patrick J. et al., Continuous Positive Airway Pressure via the Boussignac System Immediately after Extubation Improves Lung Function in Morbidly Obese Patients with Obstructive Sleep Apnea Undergoing Laparoscopic Bariactric Surgery, Anesthesiology, vol. 110, No. 4, Apr. 2009, pp. 878-884.

Nilsson et al., Age and gender do not influence the ability to detect respiration by photoplethysmography. J Clin Monit Comput. Dec. 2006; 20(6), pp. 431-436. Epub Oct. 11, 2006.

Nilsson et al., Macrocirculation is not the sole determinant of respiratory induced variations in the reflection mode photoplethysmographic signal. Physiol Meas. Nov. 2003; 24(4):925-37.

Nilsson et al., Monitoring of respiratory rate in postoperative care using a new photoplethysmographic technique. J Clin Monit Comput, 2000; 16(4):309-15.

Nilsson et al., Respiration can be monitored by photoplethysmography with high sensitivity and specificity regardless of anaesthesia and ventilatory mode. Acta Anaesthesiol Scand. Sep. 2005; 49(8). 1157-62.

Nilsson et al., Respiratory variations in the reflection mode photoplethysmographic signal. Relationships to peripheral venous pressure. Med Biol Comput. May 2003;41(3):249-54.

Oliver, Z. and V. Hoffstein, Predicting effective continuous positive airway pressure. Chest, 2000. 117(4): p. 1061-1064.

Orr, W.C. and M.L. Stahl, Sleep disturbances after open heart surgery, Am J Cardiol, 1977, 39(2): p. 196-201.

Pembrook, Linda. High Risk for Sleep Apnear Found in Pain Patients on Opioids, Issue: Jun. 2006, vol. 32.06, 3 pages.

Pilcher, D., C Scheinkestel, G Snell, A Davey-Quinn, M Bailey, T Williams. High central venous pressure is associated with prolonged mechanical ventilation and increased mortality after lung transplantation. J Thorac Cardiovasc Surg. 2005;129(4):912-8.

Pitson D, Stradling J. Value of beat-to-beat blood pressure changes, detected by pulse transit time, in the management of obstructive sleep apnea/hypopnea syndrome. Eur Respir J 1998:12:685-692.

Ramachandran et al., A Meta-analysis of Clinical Screening Tests for Obstructive Sleep Apnea, Anesthesiology; Vo. 110., No. 4, Apr. 2009, pp. 928-939.

Reeder, M.K. at al., Late postoperative nocturnal dips in oxygen saturation in patients undergoing major abdominai vascular surgery. Predictive value of pre-operative overnight pulse oximetry. Anaesthesia, 1992. 47(2): p. 110-115.

Reeder, M.K., et al., Postoperative hypoxaemia after major abdominal vascular surgery. Sr J Anaesth, 1992. 68(1): p. 23-26.

Reeder, M.K., et al., Postoperative obstructive sleep apnoea, Haemodynamic effects of treatment with nasal CPAP. Anaesthesia, 1991. 46(10): p. 849-853.

Remmers, J.E., et al., Pathogenesis of upper airway occlusion during sleep. J Appl Physiol.: Respirat. Environ. Exercise Physiol., 1978. 44(6): p. 931-938.

Rock, P. and A. Passannante, Preoperative assessment pulmonary. Anesthesiology Clinics of North America, 2004. 22(1): p. 77-91.

Rosenberg, J. and H. Kehlet, Postoperative episodic oxygen desaturation in the sleep apnoea syndrome. Acta Anaesthesiol Scand, 1991. 35(4): p. 368-369.

Rosenberg, J., et al., Circadian variation in unexpected postoperative death. Br J Surg, 1992. 79(12): p. 1300-1302.

Rosenberg, J., et al., Late postoperative nocturnal episodic hypoxaemia and associated sleep pattern. Br J Anaesth, 1994, 72(2): p. 145-150.

Rosenberg-Adamsen, et al., Postoperative sleep disturbances: mechanisms and clinical implications. Br J Anaesth, 1996, 76(4): p. 552-559.

Sabers, C., et al.: The diagnosis of obstructive sleep apnea as a risk factor for unanticipated admissions in outpatient surgery. Anesth Analg. May 2003;96(5);1328-35.

Sasse, S.A., et al., Timing of Changes in Oxyhemoglobin Saturation Resulting from Breath Holding. Sleep Medicine, 2006. 7 (S2): p. S46-S47.

Shepard JW Jr, Pevernagie DA, Stanson AW, Daniels BK, Sheedy PF. Effects of changes in central venous pressure on upper airway size in patients with obstructive sleep apnea. Am J Respir Crit Care Med. Jan. 1996;153(1):250-4.

Standards and Practice Committee of the American Sleep Disorders Association. ASDA Standards of Practice, Practice Parameters for the Use of Portable Recording in the Assessment of Obstructive Sleep Apnea.. Sleep. 1994 17(4), p. 372-377.

Teng XF, Zhang YT. The effect of contacting force an photoplethysmographic signals. Physiol Meas. Oct. 2004;25(5):1323-35.

Waldemar Carlo et al., Alae nasl activation (nasal flaring) decreases nasal resistance in preterm infants. Pediatrics vol. 72, Issue 3, pp. 338-343.

Warner, David S. et al., Obstructive Sleep Apnea of Obese Adults, Anesthesiology, vol. 110, No. 4, Apr. 2009, pp. 908-921.

Westbrook P. et al. Predicting Effective Continuous Positive Airway Pressure (CPAP) based on Laboratory Titration and Auto-titrating CPAP, 8th World Congress on OSA. Sleep Medicine, vol. 7, Suppl. 2, 2006, 2 pages.

Westbrook P, et al. Predicting Treatment Outcomes for Oral Appliance Therapy for Sleep Apnea using Pre-treatment In-home Sleep Studies, 8th World Congress on OSA. Sleep Medicine. vol. 7, Suppl. 2. 2006. p. 1-2.

Westbrook, P., et al. Validation of an Apnea Risk Evaluation Questionnaire. In American Thoracic Society International Conference. 2005. San Diego, CA. 2 pages.

Westbrook, P., et al., Description and Validation of the Apnea Risk Evaluation System: A Novel Method to Diagnose Sleep Apnea-Hypopnea in the Home. Chest, 2005. 128(4): p. 2166-2175.

Wilson, Kerryn et al., Can Assessment for Obstructive Sleep Apnea Help Predict Postadenotonsillectomy Respiratory Complications; Anesthesiology, vol. 96, No, 2 Feb. 2002, pp. 313-322.

Young, T., et al., Epidemiology of Obstructive Sleep Apnea: A Population Health Perspective. Am J Respir Crit Care Med, 2002. 165(9): p. 1217-1239.

\* cited by examiner

SYSTEM FOR THE ASSESSMENT OF SLEEP QUALITY IN ADULTS AND CHILDREN

RELATED APPLICATION

This application claims the benefit of U.S. provisional patent application Ser. No. 61/160,924 entitled "SYSTEM FOR THE ASSESSMENT OF SLEEP QUALITY IN ADULTS AND CHILDREN," filed on Mar. 17, 2009, which is incorporated herein by reference in its entirety.

FIELD OF THE INVENTION

The present invention generally relates to the field of monitoring sleep architecture and more specifically to systems and methods for assessing the sleep quality of adults and children.

BACKGROUND

Sleep is essential for survival and poor sleep quality is a principal contributor to chronic diseases. Typically an individual has four to six sleep cycles per night, each between 60 and 120 minutes in length and comprising of different proportions of rapid eye movement (REM) sleep and non-REM sleep (that is further divided into stages N1, N3 and N3). Each sleep cycle typically begins with non-REM sleep and ends with REM sleep. The first half of the night contains most of the N3 or slow wave sleep (SWS), whereas rapid eye movement (REM) sleep is most prominent in the second half. SWS is considered the deepest and most restorative of sleep stages during which there is a reduction in heart rate, blood pressure, sympathetic nervous activity, and brain glucose metabolism, and increase in vagal tone. Hypothalamo-pituitary-adrenal activity is suppressed during SWS and increased during REM sleep. The sequence of sleep stages (NREM sleep stages 1, 2, 3 or the REM sleep stage) during an (overnight) sleep or (daytime) nap, sometimes interrupted with brief periods of wakefulness, is referred to as sleep architecture.

Poor sleep quality resulting from sleep fragmentation or abnormal sleep architecture alters the proportion of REM, non-REM and SWS obtained per night. When a normal individual is chronically sleep deprived, the onset of REM in the first sleep cycle is faster and the total amount of REM and SWS changes. The amount of lighter stages of NREM sleep (stage N1) is decreased. In contrast to this sleep deprivation in a healthy individual, there are a number of medical conditions that contribute to repetitive arousals during the night. This leads to sleep fragmentation and a different sort of chronic inadequate sleep. The frequency of the arousals and their impact on sleep disruption is dependent both on the sleep stage when the arousal occurs and one's susceptibility to sleep disturbances. Individuals are least likely to have arousals or to awaken from an arousal during SWS and most likely during stage N1 NREM and REM sleep. Frequent arousals can disrupt sleep architecture with patterns of awakening that limit the amount of REM and slow wave sleep. Chronic inadequate sleep also manifests in patients who suffer from an inability to easily fall asleep or maintain sleep throughout the night. The assessment of sleep architecture is useful to physicians trying to determine the appropriate diagnosis. For example, in major depression, patients exhibit increased sleep latency, frequent arousals, difficulty remaining asleep, and decreased in slow wave sleep. The first episode of REM sleep will appear earlier than usual, with an increase in total percentage of REM sleep, longer duration REM sleep periods, and increased eye movement density (referred to as REM sleep disinhibition). Patients with post-traumatic stress syndrome can also exhibit abnormal sleep architecture i.e., an increase the amount of REM sleep per night, similar to depressed patients.

Neurological signals i.e., electroencephalograph (EEG) and/or electrooculargram (EOG) are extremely sensitive to the measurement of sleep stage/sleep architecture and sleep quality but fairly insensitive in the assessment of sleep disordered breathing. The detection of arousals during sleep can be measured by multiple means including cortical (i.e., EEG, sympathetic (e.g., electrocardiograph (ECG), pulse rate or peripheral arterial tone), or behavioral (e.g., changes in respiration, movement or position, etc.) approaches. Cortical arousals measured by EEG is the gold-standard measure of sleep disturbance/fragmentation although the reliability of visual scored events may be less sensitive than beat-to-beat changes in cardiac function. The frequency and duration of the arousal, its temporal association with breathing, and the position of the head when the arousal occurs all provide information useful in differentiating the underlying medical condition. For menopausal related sympathetic arousals, the gradual increase in core body temperature that results in a hot flash precedes the arousal during non-REM sleep while the hot flash follows the awakening during REM sleep. The intensity and timing of the hot flash can impact the ability to return to sleep and contributes to sleep maintenance insomnia.

Respiratory effort related arousals are triggered by a full or partial collapse of the upper airway (i.e., sleep disordered breathing or Obstructive Sleep Apnea (OSA)) as a response to return airway patency. The contribution of OSA to poor sleep quality increases the risk of accidents due to daytime drowsiness and has been associated with hypertension, increased risk of congestive heart failure, coronary artery disease, myocardial infarction, cardiac arrhythmias, asthma, diabetes and stroke.

Abnormal subcortical motor system activation associated with periodic limb movements or restless leg syndrome in adults and children can result in arousal sequences similar to OSA that compromise sleep quality and cause sleep deprivation. Environmental conditions such as noise i.e., snoring bed partner, passing vehicles, etc. or sleeping away from home can contribute to delayed sleep onset, abnormal sleep architecture, and increased susceptibility to arousals.

Conventional focused respiratory- or cardio-based approaches are highly sensitive to breathing-related sleep disordered such as OSA but relatively insensitive to the assessment of sleep architecture or sleep quality. In conventional techniques, respiration is measured by multiple means, including airflow, respiratory effort, and/or ECG-related changes. While the most accurate and direct method of monitoring respiratory effort is by measurement of changes in intrathoracic pressure by use of an esophageal catheter, this procedure is invasive and not well tolerated by the patient. Respiratory effort is most commonly measured with bands placed around the chest and abdomen to assess breathing-related change in compartmental circumference. Pulse transit time (PTT) measures the time it takes for a pulse pressure wave to travel from the aortic valve to the periphery. The electrocardiographic (ECG) r-wave is used as the start-time, and the arrival of the pulse at the finger reflects the blood pressure fluctuations induced by negative pleural pressure swings. Diaphragmatic electromyography (EMG) provides a fourth measurement of inspiratory effort and has been shown to have a good correlation with increases in esophageal pressure. Changes in forehead venous pressure represent a new approach that has been shown to measure changes in respiratory effort.

The measurement of airflow is routinely performed by affixing a pressure transducer to a nasal cannula positioned in the nostrils. When a cannula is used measure nasal pressure, the portion inside the nose act as a resistor, and the pressure drop between the nasal cavity and the atmosphere acts like a crude pneumotachometer. The positioning and displacement of the cannula tips inside the nostrils, the size of the nasal openings, and whether the subject is mouth breathing impact the amplitude and shape of the nasal pressure signal. Amplitude variability is less problematic when visual scoring is employed, however amplitude changes can be problematic with mathematically-based measures of tidal volume changes. An advantage of nasal pressure airflow (vs. thermistor or sound-based flow measures) is that shape of airflow signal can be evaluated to assess flow limitation.

Chronically poor sleep quality and associated reduction in SWS results in decreased insulin sensitivity, reduced glucose tolerance and increased risk of type 2 diabetes. Poor sleep quality resulting from menopausal hot flashes is associated with insomnia, depression, anxiety, mood disorders, and cognitive and memory impairment. Low sleep efficiency, abbreviated total sleep time and shortened REM sleep times contributes to the severity of drug-resist hypertension. Sleep deprivation causes an imbalance between leptin and ghrelin (opposing metabolic counterparts which control hunger and food intake) and leads to increased consumption of high carbohydrate foods, weight gain, and obesity. Poor sleep quality unrelated to sleep disordered breathing has been associated with chronic, low-grade inflammation in otherwise healthy young women which increases the risk of future adverse health outcomes. Increased inflammatory markers were found to be sleep duration dependant in women, but not men. Poor sleep quality has explained elevated levels of Interleukin-6 (IL-6), a pro-inflammatory cytokine associated with sleep apnea, narcolepsy, insomnia, excessive daytime drowsiness and fatigue. Elevated IL-6 was strongly associated with decreased sleep efficiency, increased REM latency, and percentage of waking incidences after sleep onset. Other inflammatory markers, such as C-reactive protein are also associated with similar sleep disturbances associated with sleep apnea, and interactions of sleep disturbances and C-reactive protein are associated with cardiovascular diseases. Elevated inflammation is associated with many diseases, including cancer, cardiovascular disease, hypertension, chronic fatigue syndrome, fibromyalgia, depression, and autoimmune disorders among others. Elevated inflammatory cytokines (and other inflammation markers, such as C-reactive protein) are associated with earlier onset of disability in the elderly, increased risk of cardiovascular disease and hypertension, as well as increased risk of diabetes and metabolic X syndrome. In these disease states, elevated inflammation interacts with sleep disturbances in a bi-directional manner to exacerbate the disease state.

It is not uncommon for patients to be misdiagnosed due to overlapping co-morbid symptomology (e.g., untreated OSA to be misdiagnosed as insomnia). Older women are particularly susceptible to misdiagnosis because of the increased risk of OSA as progesterone levels decline and the assumption that menopausal related symptoms are the source of the depressed state or reported problem with sleep. Conversely, patients may be misdiagnosed with OSA when the sleep fragmentation related to the number of cortical or sympathetic arousals is disproportionately greater than a mild case of obstructive breathing event. The overlapping behavioral symptomology of childhood OSA, limb movements during sleep, and Attention Deficit/Hyperactivity Disorder (ADHD) provide other examples where of the difficulty of a differential diagnoses, particularly for a pediatrician with only general knowledge regarding these disorders. Accurate characterization of the etiology of poor sleep quality requires measurement of signals that reflect respiratory, cardiological, and neurological physiology. Thus, it would be useful to simply and easily acquire all sets of measures and combine this information with medical history information and a database of responses to assign pre-test probabilities and/or assist clinicians in constructing their differential diagnoses.

SUMMARY

Systems and methods for assessment of sleep quality in adults and children are provided. The assessment of sleep quality includes performing concurrent measurements of two categories of signal data: (1) signal data related to sleep states, and (2) signal data related to a type of sleep disruption (also referred to herein as "arousals"). The type of sleep disruption can be used to help diagnose what may be causing poor sleep quality in a patient. These techniques include an apparatus worn above the forehead containing the circuitry for collecting and storing physiological signals. The apparatus can be integrated with or connected to a sensor strip and can also integrate with or be connected to a nasal mask to obtain the physiological signals for the user. The form factor of this apparatus is comfortable, easy to self-apply, and results in less data artifacts than conventional techniques for capturing physiological data for analyzing sleep quality. Neuro-cardio-respiratory signals are analyzed using means to extract more accurate definitions of the frequency and severity of sleep discontinuity, sleep disordered breathing and patterns of sleep architecture. Biological biomarkers and questionnaire responses can also be compared to a database of healthy and chronically diseased patients to provide a more accurate differential diagnosis and to help determine the appropriate disease management recommendations.

Neuro-respiratory signals are analyzed to extract more accurate definitions of the frequency and severity of sleep discontinuity, sleep disordered breathing and patterns of sleep architecture.

According to an embodiment, a system for assessing sleep quality of a user is provided. The system includes a sensor strip comprising at least one sensor configured to detect data indicative of sleep disturbances of a user. The sensor strip is positioned on the user's forehead. The system also includes a wearable data acquisition unit coupled to the sensor strip. The data acquisition unit is configured to receive and collect data from the sensors in the sensor strip.

According to another embodiment, a system for assessing sleep quality of a user is provided. The system includes a wearable data acquisition unit for concurrently measuring data indicative of a sleep state of a user and indicative of sleep disturbances experienced by a user. The system also includes a sensor strip coupled to the data acquisition unit. The sensor strip includes at least one sensor configured to detect a psychophysiological data of the user and to provide the data to the data acquisition unit. The data acquisition unit is configured to receive data from the sensors in the sensor strip.

According to yet another embodiment, a system for assessing sleep quality of a user is provide. The system includes a sensor strip that includes at least two sensors sensors configured to detect data indicative of sleep disturbances of a user, and a wearable data acquisition unit coupled to the sensor strip. The at least two sensors are configured to collect data of a different type, and the sensor strip is removably affixed to the user's body. The data acquisition unit is configured to receive and collect data from the sensors in the sensor strip.

DETAILED DESCRIPTION

Systems and methods for the assessment of sleep quality in adults and children are provided. The assessment of sleep quality includes performing concurrent measurements of two categories of signal data: (1) signal data related to sleep states, and (2) signal data related to a type of sleep disruption (also referred to herein as "arousals"). These techniques system allow clinicians to more accurately relate sleep quality with the underlying disease/disorder. Given the substantial night to night variability in physiology, the patient's home is the preferred environment for acquiring multiple night studies. Thus, embodiments use electrodes and sensors that can be self-applied with limited skin or scalp preparation, and which monitors signal quality during use and provides user feedback when signal quality problems are detected.

The techniques disclosed herein provide a benefit over conventional techniques for monitoring sleep quality, by concurrently collecting data related to sleep architecture and sleep disruption using a compact and easy to use system that can be employed in a user's home. Conventional techniques require that patients be monitored at a sleep laboratory, where patients often have trouble sleeping well. Some conventional techniques can be used by patients in the home, but they are harder for the patient to use and do not allow for concurrent collection of data related to sleep architecture and sleep disruption.

Figure 1:
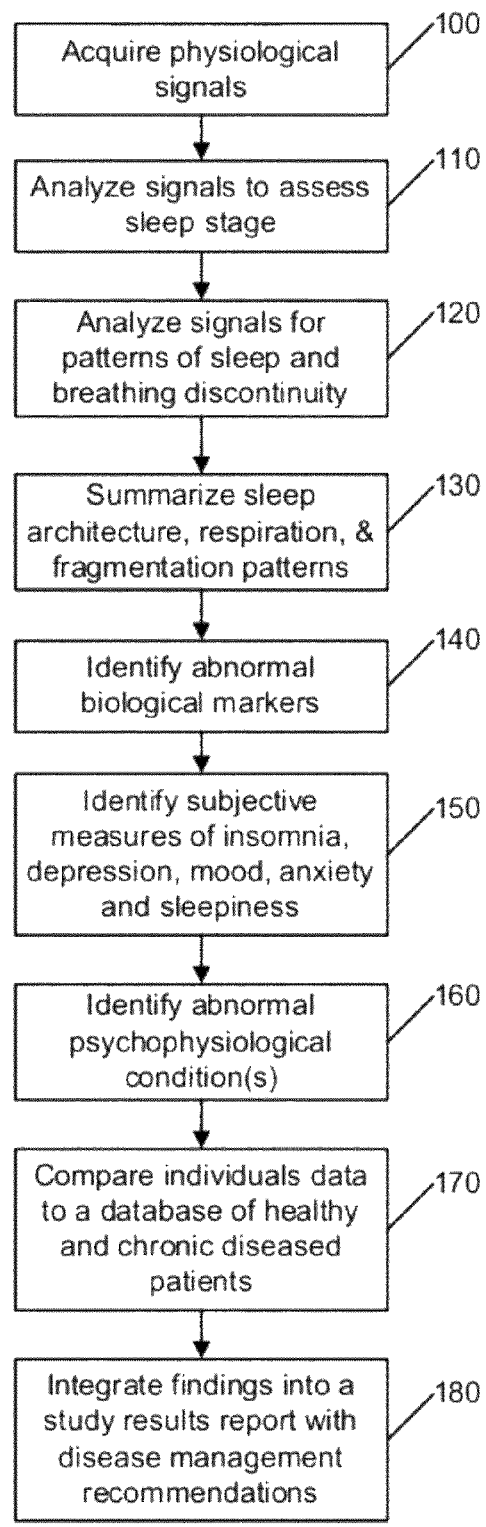
FIG. 1 is a flow diagram of the method for assessing sleep quality according to an embodiment.

FIG. 1 is a flow diagram of the method for assessing sleep quality according to an embodiment. The method can be used to assess the severity and impact of poor sleep quality. FIG. 1 will be discussed in detail below after introducing various embodiments of systems that can be used for implementing this method.

Figure 2B:
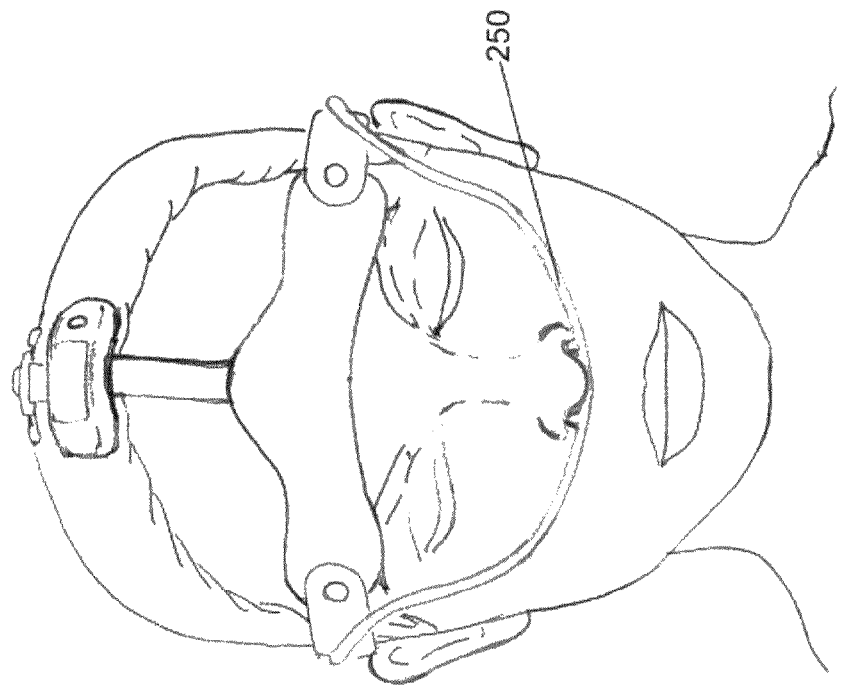
FIGS. 2A and 2B illustrate a patient with the data acquisition system including the data acquisition unit, sensor strip, and nasal mask and nasal cannula according to two embodiments.
Figure 2A:
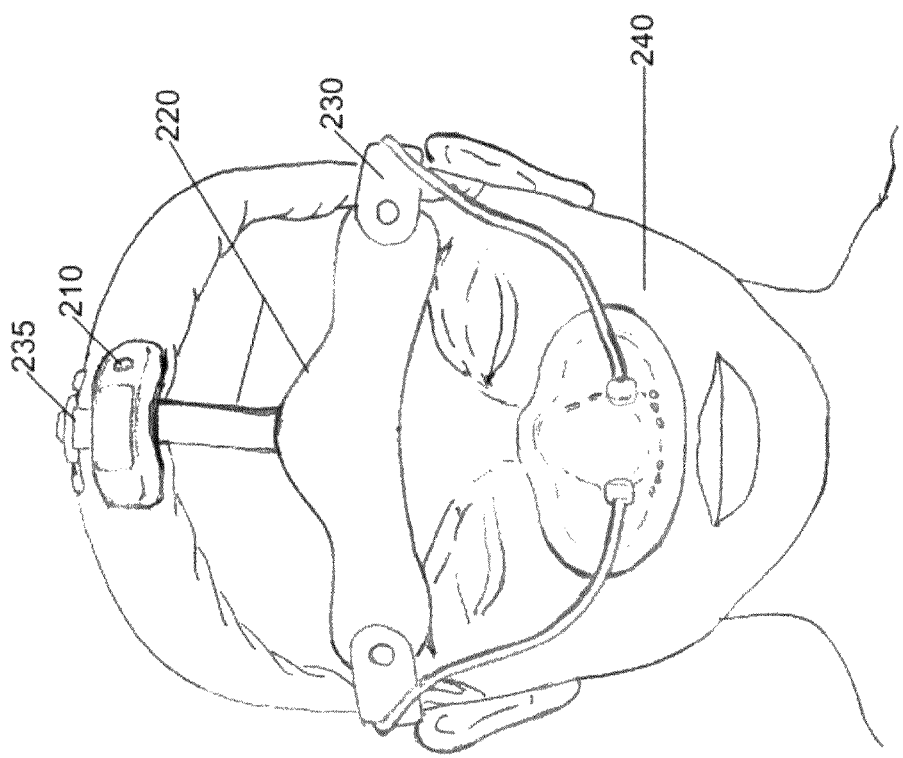

FIGS. 2A and 2B illustrate a patient with the data acquisition system including the data acquisition unit, sensor strip, and nasal mask and nasal cannula according to two embodiments. The data acquisition system can be used to collect and store physiological signals from a user while the user is sleeping in order to assess sleep quality. According to an embodiment, the data acquisition system can connect to an external computer system that is configured to process the data collected by the data acquisition system (see FIG. 3 described below). In some embodiments, the data acquisition system can be configured to perform at least some analysis on the data collected before the data is downloaded to the external computer system.

Figure 5:
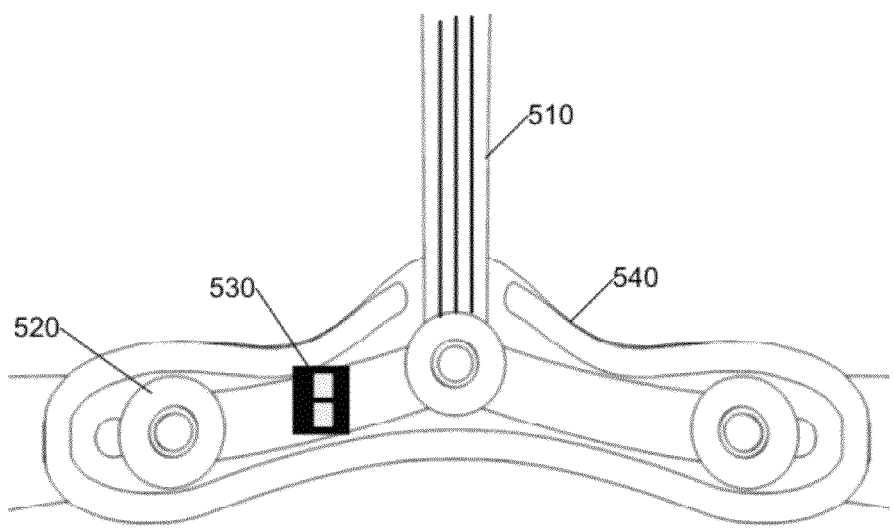
FIG. 5 is an illustration of the integrated sensor strip of FIGS. 2A and 2B used to acquire physiological signals according to an embodiment.
Figure 7A:
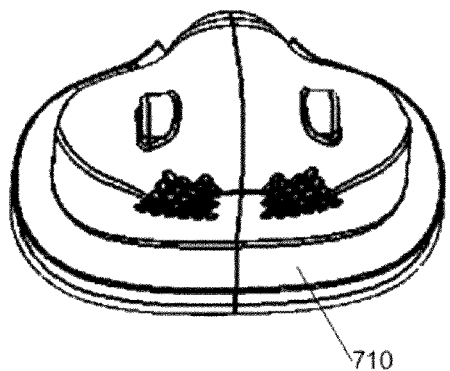
FIGS. 7A, 7B, and 7C illustrate views of a disposable nasal mask capable of obtaining minute changes in airflow according to an embodiment.
Figure 7B:
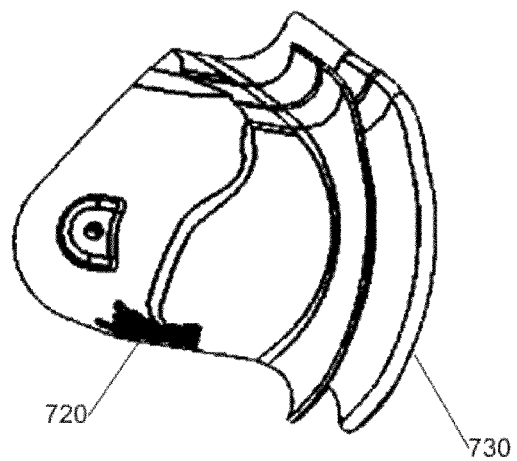
Figure 7C:
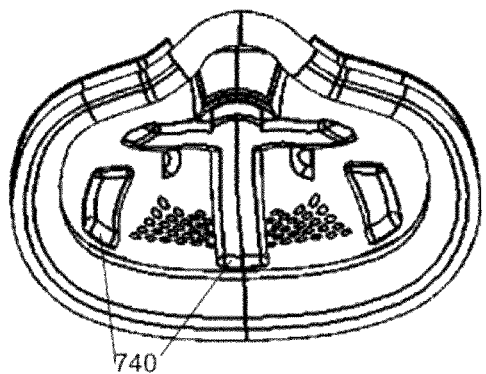

Data Acquisition Unit (DAU) 210 is worn above the forehead of the user during sleep to collect physiological signal data. In the embodiment illustrated in FIG. 2A, the DAU 210 is integrated or coupled with a sensor strip 220 and a nasal pneumotachometer 240. FIG. 5, described below, illustrates an embodiment of the sensor strip 220, and FIGS. 7A, 7B, and 7C illustrate several views of an embodiment of nasal pneumotachometer mask 240. In the embodiment illustrated in FIG. 2B, an alternative arrangement that includes a nasal cannula 250 is provided. A headband 230 encircles the rear of the patient's head to hold the data acquisition system in place. A top strap 235 also extends over the back of the patient's head where it joins the headband 230 for additional stability. Sensor strip 220 can be coupled to headband 230 to hold the sensor strip 220 in place over the user's forehead.

According to an embodiment, the headband 230 and/or the top strap 235 can be adjusted in size to accommodate users having different sized heads. In some embodiments, can be removed and replaced with different sized headbands and top straps to accommodate different users. Furthermore, the headband and top straps can be designed to be one-time-use components for sanitary purposes that can be removed while allowing the data acquisition unit and/or other components of the apparatus to be used by another user.

In an embodiment, the DAU 210 includes physiological acquisition and storage circuitry configured to assess sleep quality or record data for use in assessing sleep quality. As described above, the assessment of sleep quality includes performing concurrent measurements of two categories of signal data: (1) signal data related to sleep states, and (2) signal data related to the type of sleep disruption. DAU 210 is configured to perform the concurrent measurements of the sleep data, record these measurements, and in some embodiments, analyze and process the recorded data. The DAU 210, sensor strip 220, and headband 230 can be used to implement the method illustrated in FIG. 1. According to some embodiments, DAU 210 can be positioned near the top of the head of the user (as illustrated in FIG. 2) or positioned over the forehead of the user. The position of the DAU 210 can be based in part on the type of assessment to be performed and the types of sensor data used to make that type of assessment.

According to an embodiment, sensor strip 220 is removable, and in some embodiments, sensor strip 220 can also be disposable. For example, the sensor strip 220 can be configured to be electronically coupled to the DAU 210 using a socket connection or other type of connection that allows the sensor strip 220 to be removed and replaced. This can allow the sensor strip to be replaced for sanitary purposes (as well as the top strap and/or the headband, as described above) to allow the DAU 210 to be used again with another user. In an embodiment, the sensor strip 220 can be a one-time-use strip that is provided in a sealed sterile package. In some embodiments, elements of sensor strip 220 can be disposable, while some components are reusable. For example, the sensor strip 220 may include disposable EEG sensors and a reusable the pulse/oximetry sensor. One skilled According to an embodiment, sensor strip 220 can also include an adhesive backing that helps to facilitate and maintain placement of the sensor strip 220 on the user's forehead region by removeably adhering to the user's skin. In one embodiment, the sensor strip 220 can comprise adhesive backed foam. The adhesive backing can also help to maintain sensor contact with the user's skin for those sensors that require skin contact. According to some embodiments, conductive sensors included in the sensor strip 220 can have a conductive gel placed over theses sensors. FIG. 5, described below, illustrates some example of the types of sensors than be included in the sensor strip 220. The configuration of the sensor strip 220 facilitates use of the data acquisition system at home by users by making proper placement and attachment of sensors much easier than conventional systems. For example, some conventional EEG monitoring systems require that numerous electrodes be affixed to a patient's head. Proper placement of the electrodes is important. As a result, EEG data is often gathered in a clinical setting where the electrodes can be affixed to the patient by a clinician. When performing sleep studies, this can have a negative impact on the results of the study, because the user is removed from his or her normal sleeping environment and placed into an unfamiliar clinical setting. The sensor strip 220 used with the data acquisition systems disclosed herein facilitates home use of the device by making proper placement of the sensors easy for patients, thereby allowing users to gather data at home where they are likely to be more comfortable and more likely to experience sleep episodes that are more typically of their regular sleep episodes.

Figure 3:
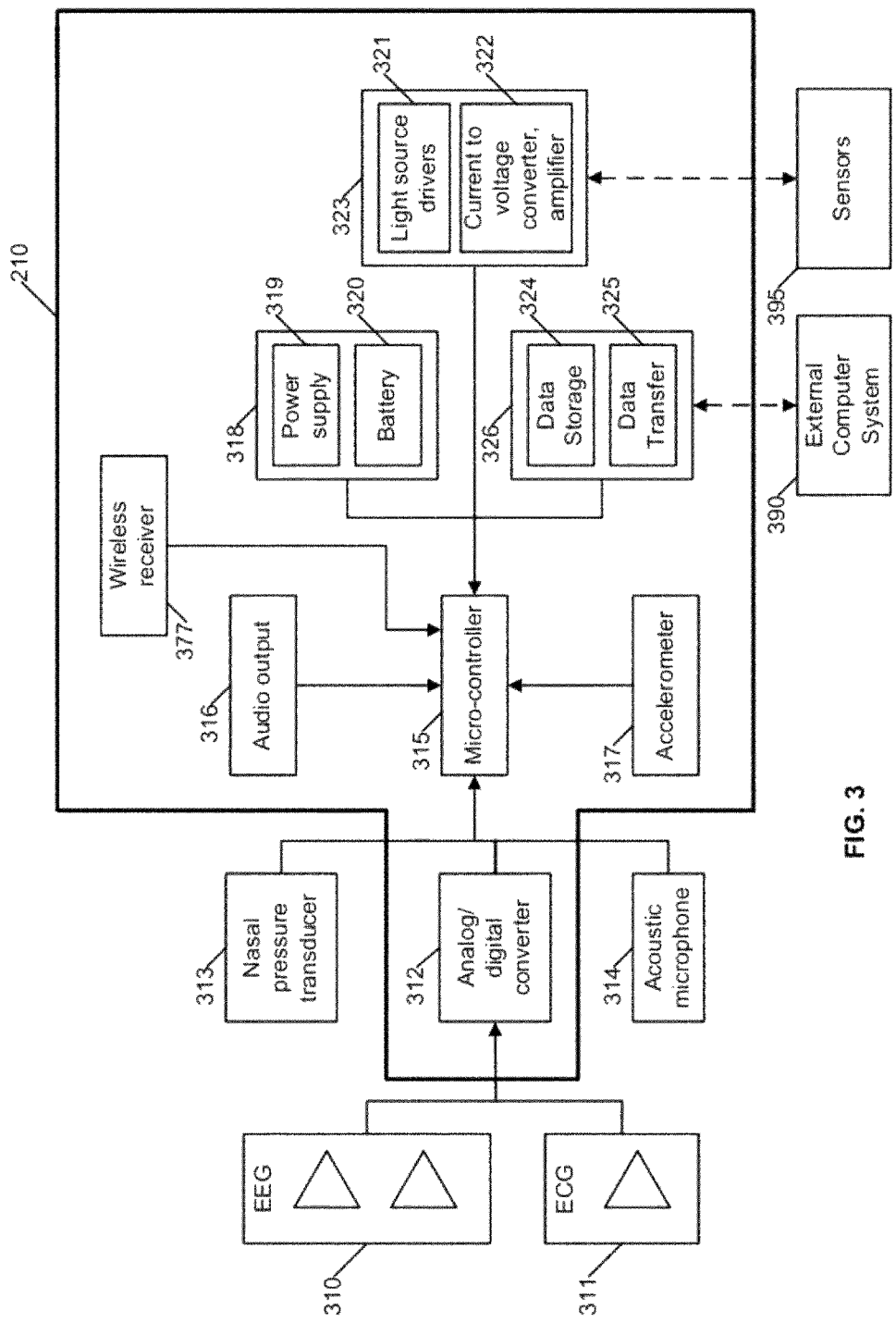
FIG. 3 is a block diagram identifying functional components and circuits of a data acquisition apparatus for quantifying sleep quality according to an embodiment.

FIG. 3 is a block diagram identifying functional components and circuits of a data acquisition apparatus for quantifying sleep quality according to an embodiment. As described above, the assessment of sleep quality includes performing concurrent measurements of two categories of signal data: (1) signal data related to sleep states, and (2) signal data related to the type of sleep disruption. The DAU 210 includes an analog-to-digital converter 312 for amplifying and digitizing two channels of EEG/EOG data 310 for measuring sleep architecture and cortical arousals, and one channel of ECG data 311 to assess heart rate and autonomic/cortical arousals. According to other embodiments, any combination of EEG channels could be employed. However, a single channel of EEG can reduce the accuracy of the sleep stage measurement and more than two channels can increase the size of the DAU without significantly increasing detection accuracy. The use of two channels can significantly increase the system's ability to differentiate REM from NREM sleep on the basis of rapid conjugate eye movements that are characteristic of REM sleep and appear as large voltage deflections that are out of phase in the two EEG channels. According to an embodiment, the EEG/EOG data 310 and EEG data can be captures using electrodes integrated into sensor strip 220. FIG. 5, which is described in detail below, provides an example embodiment of one possible configuration of the sensor strip 220 that includes EEG/EOG/EMG electrodes for gathering the EEG/EOG data 310 and the ECG data 311.

DAU 210 is configured to receive a signal from a pressure transducer 313 to acquire airflow data. The airflow data can be used in identifying sleep disruptions, such as apnea. In a preferred embodiment the dynamic range of the pressure transducer is set to optimize airflow resolution of (i.e., +/−2 cm/H20).

Acoustic microphone 314 can also be used to detect snoring and/or other audible symptoms that can be causing sleep disruption. DAU 210 includes an amplification circuit that receives and amplifies sound signals from acoustic microphone 314. In some embodiments, the acoustic microphone 314 can be integrated into the DAU 210, while in other embodiments, the acoustic microphone 314 can be included in the sensor strip 220 or affixed to the headband 230. In a preferred embodiment, a high fidelity sound is sampled between 2 to 4 kilohertz to profile snoring pattern and to recognize the region of airway obstruction as well as assess nocturnal coughing and wheezing. Alternatively, in some embodiments, snoring sounds can be quantified by rectification, integration, and sampling at a reduced frequency (e.g., 10 Hz) or with sensors limited to qualitative measures (e.g., vibration).

The DAU 210 includes an accelerometer 317 that can measure a full range of head positions, including both sleep and wake conditions, as well as behavioral arousals defined by subtle head movements.

In the embodiment illustrated in FIG. 3, the DAU 210 includes a battery power component 318 that includes a rechargeable lithium polymer battery 320 and a power supply and recharging circuitry 319 for receiving power from an external source for recharging battery 320 and/or powering the DAU 210. The battery power component 318 allows the DAU 210 to operate without requiring the DAU 210 to be tethered to an external power cord or power supply, which could be inconvenient and uncomfortable for a user of the device. According to some embodiments, an external power supply can be used to power the device. According to other embodiments, battery 320 can be another type of battery 320 and in some embodiments battery 320 can be removable and replaceable.

A sensor driving unit 323 is included to provide a driving current to drive red and infrared light emitting diodes used in conjunction with sensors 395 to gather physiological data. The DAU 210 also includes an optical signal amplifier that includes digitally programmable potentiometers 321 and a means to convert and amplify outputs from a photodiode 322. According to an embodiment, the sensors 395 can be included in the sensor strip 220.

The DAU 210 can include a memory 324 for data storage. In an embodiment, the memory 324 can comprise a removable Multimedia Memory or Secure Digital card or other types of removable persistent memory. In another embodiment, the memory 324 can comprise a fixed flash chip. According to an embodiment, a data transfer interface 325 is provided. According to an embodiment, the data transfer interface comprises a USB data transfer chip. In another embodiment, USB transfer capabilities can be incorporated into micro-controller 315.

According to an embodiment, firmware is stored in a memory 317 associated with micro-controller 315. According to an embodiment, the memory 317 is a flash memory. According to some embodiments, the firmware 317 can be updated via data transfer interface 325. Furthermore, according to some embodiments, the memory 317 and the memory 324 can be part of the same persistent memory.

In an embodiment, the firmware is configured to routinely sample and save signal data received by the DAU 210. According to an embodiment, filtering routines can be used to detect poor quality signal data and to notify the user via an audible signal generated using audio speaker 316 or via a piezo-electric buzzer. For example, if the user has misaligned the position of the sensor strip 220 on the forehead, the signals received from the sensor strip may of poor quality. The DAU 210 can generate an audible alarm or vibrate if the sensor strip needs to be realigned.

In a preferred embodiment the airflow signal is monitored when it is acquired, either by flow amplitude or flow volume to ensure the device has been properly applied and being worn correctly. In one embodiment, thresholds are applied to the mean and standard deviation of the airflow amplitude across overlapping time windows (i.e., 5 minutes) to identify reductions associated with an interface leak. However, in other embodiments, other measures of low airflow can be performed, including but not limited to tidal volume, root mean squared or integrated measures, or derivations from band pass filters. According to an embodiment, the EEG/EOG and ECG signals are monitored for high input impedance, 60 Hz noise, or spikes in the signal to identify when signal quality is poor. In an embodiment, the signals obtained with a reflectance sensor are filtered and monitored to ensure the reflectance sensor is properly positioned for acquiring oximetry.

In one embodiment, DAU 210 can include a wireless transmitter/receiver 377 for receiving data from peripheral sensors (i.e., wireless ECG sensors, finger pulse oximeter, respiratory effort bands, sensors measuring leg movements, etc.) and/or transmit signals to an external computer system 390 for real time monitoring of the data being acquired by the DAU 210. Data acquired from these sensors can be used to determine the user's sleep architecture and/or to identify sleep disruptions that can negatively impact sleep quality. In some embodiments, the wireless transmitter/receiver 377 can be integrated into data transfer module 326 of DAU 210.

According to an embodiment, micro-controller 315 can be based on an ARM 32-bit reduced instruction set computer (RISC) instruction set or equivalent architecture. Firmware can be configured to minimize the power requirements of the ARM chip when the DAU is being used in recording mode. The computational capacity of the ARM chip can provide the option for firmware to transform the signals during acquisition or prior to data download. For example, fast-Fourier transforms can be applied to a 512 samples/second EEG signal can quantify the high frequency power spectral densities of the EEG or EMG without requiring the large data files to be transferred off line to make this computation. Once high resolution power spectra are computed the EEG can be saved at 64 samples/second for purposes of visual inspection. Given the preference to obtain high fidelity sound signals, in some embodiments it would be beneficial the two-kilohertz signal can be pre-processed and down sampled to reduce data transfer time without compromising analytical power. This approach to down-sampling significantly reducing the size of and time to transfer data files from the DAU 210 to an external computer system 390 for analysis. In alternative embodiments, a lower-powered micro-controller is used when the DAU is used as a recorder. The micro-controller and also include features such as a temperature monitor, analog to digital converter, and/or the capability to transfer the data file in USB format to reduce the need for extra components.

Figure 13:
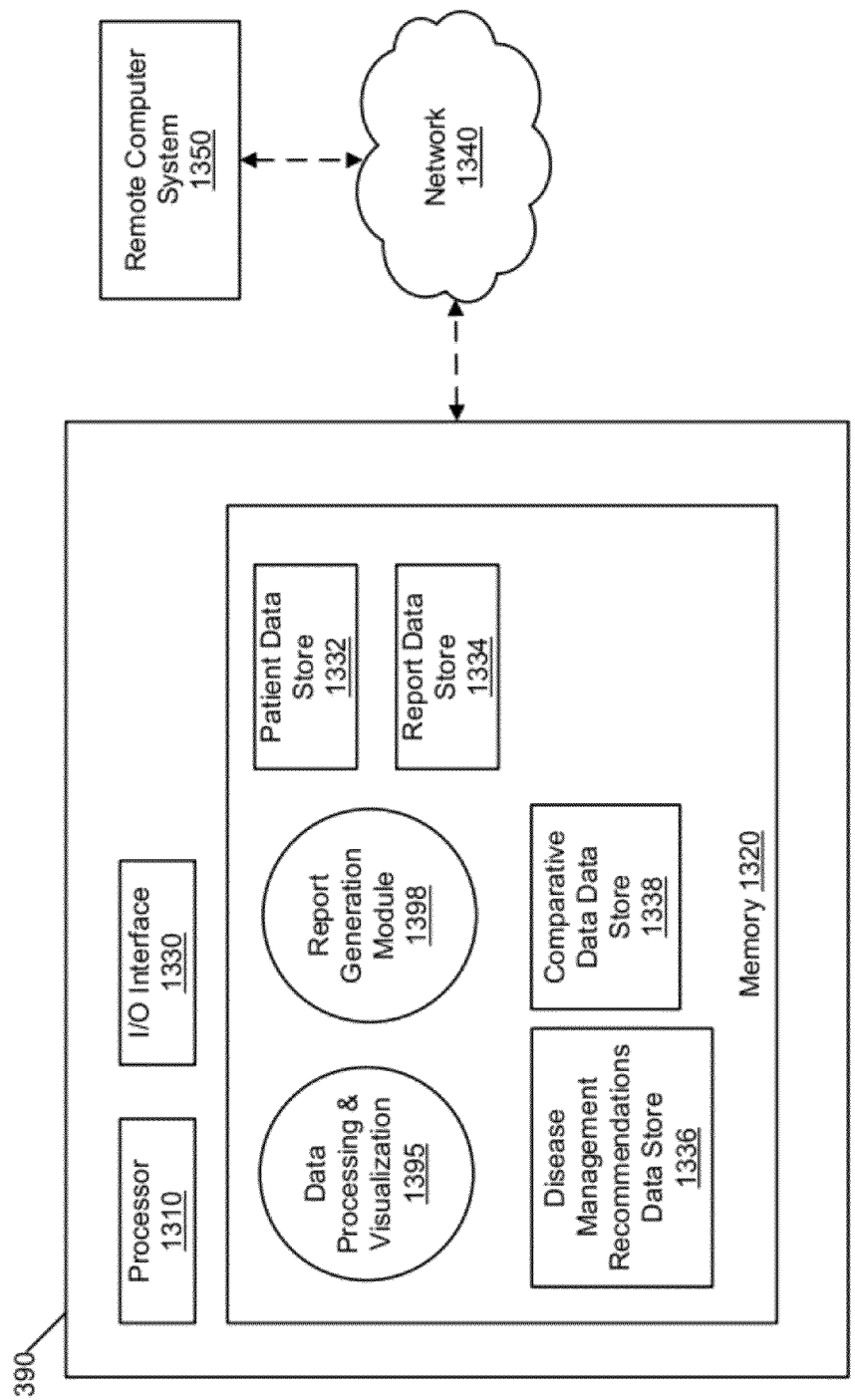
FIG. 13 illustrates an exemplary computer system that can be used in conjunction the DAU according to an embodiment.

FIG. 13 illustrates an exemplary computer system that can be used in conjunction the DAU 210 according to an embodiment. In some embodiments, the external computer system 390 is a user's home computer system. In other embodiments, the external computer system 390 is a doctor's computer system. For example, a doctor wishing to perform a sleep assessment on a patient can issue a DAU 210 to the patient. The patient can then use the DAU 210 at home to capture sleep related data and return the DAU 210 to the physician who can then download the data from the DAU 210 in order to assess the sleep quality of the patient.

External computer system 390 can include an I/O interface for communicating with the data transfer module 326 of DAU 210. According to some embodiments, the external computer system 390 can interface with the DAU 210 using either a wired or a wireless interface. In an embodiment, the DAU 210 can download information to the external computer system 390 for analysis, receive firmware updates from external computer system 390, and/or receive configuration data for configuring the operation of the DAU 210. External computer system 390 includes a processor 390 for executing computer-software instructions, and a memory 320 can be used to store executable software program modules that can be executed by the processor 1310 of external computer system 390.

According to an embodiment, DAU 210 can be configured to perform various processing on the data collected from the sensors and to download the processed data to external computer system 390. According to some embodiments, the DAU 210 can capture and store data from the various sensors and the data is downloaded to external computer system 390 for processing. As described above, the DAU can include firmware that performs at least a portion of the processing of the signal data collected before the data is downloaded to the external computer system 390.

According to an embodiment, the external computer system 390 can include a data processing and visualization module 1395 that can be used to view data collected and/or analyzed by DAU 210 and/or perform analysis and processing on the data. According to an embodiment, the external computer system 390 can also include a reporting module 1398 for generating reports based on the data collected by the DAU 210.

According an embodiment, the external computer system 390 can include a patient data store 1332, a reporting data store 1334, a disease management recommendations data store 1336, and a comparative data data store 1338. In an embodiment, the data stores can be relational databases or other types of persistent and searchable data stores in memory 1320 of computer system 1320. According to some embodiments, one or more of the data stores can be stored on an external server and can be accessed by external computer system 390 via a network connection.

The patient data store 1332 stores patient related data, e.g. a patient identifier and/or patient demographic information. Patient data from the patient data store 1332 can be used in the various assessments described here for assessing the sleep quality of the user. The reporting data store 1334 can be used to store reports generated by the report generation module 1398 and can also include report templates that can be used to determine the format of the report and/or the types of analysis to be included in the reports. The disease management recommendations data store 1336 can be used to store various treatment recommendations that can be included in patient reports based on the analysis of the data gathered by the DAU 210. The comparative data data store 1338 can be used to store comparative data from healthy patients and/or patients with a chronic illness that causes sleep quality to degrade. The comparative patient data can be used, in part, to assess the sleep quality of a patient by providing a baseline of healthy and ill patients against which a user's data can be compared.

Figure 4:
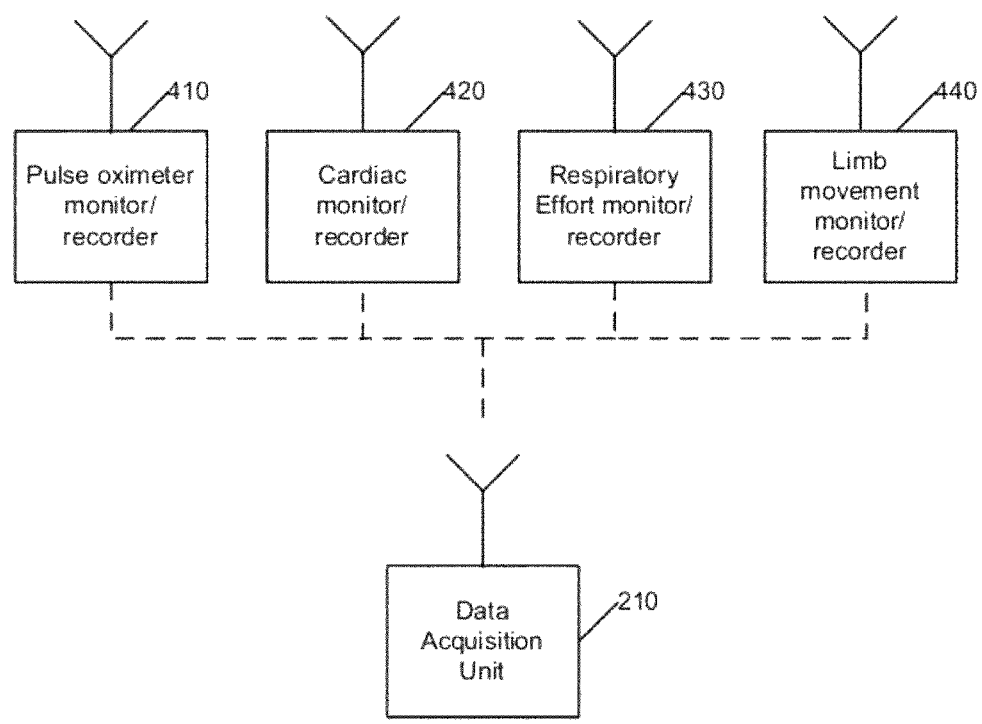
FIG. 4 is a block diagram of integrated wireless sensors affixed to different locations on the body for acquiring the physiological signals according to an embodiment.

According to an embodiment, external computer system 390 can be a user's home computer system, and the DAU 210 can include software for downloading data captured by the DAU 210 and/or the sensors interfaced with the DAU 210 to a remote computer system 1350 via a network 1340. For example, in an embodiment, the DAU 210 can include software that periodically connects to external computer system 390 via a wireless interface, downloads data from the DAU 210 to the external computer system 390, and triggers a transfer of the data from the external computer system 390 to a remote computer system, such as a doctor's computer system or a web portal. In an embodiment, the remote computer system can be a web portal comprising one more remote servers that can collect and analyze data received from DAU units. For example, a doctor treating a patient can create an account on the web portal for that patient and associate the account with a particular DAU 210. The patent can then use the DAU 210 to capture data FIG. 4 illustrates how DAU 210 can be integrated with one or more wireless sensors for measuring various physiological data that can be used to identify sleep disruptions. For example, sensor 410 comprises wireless sensors used to measure pulse/oximetry from the finger, sensor 420 comprises a device that obtains electro-cardiographic signals (e.g., holter monitor), sensor 430 comprises respiratory effort belt, and sensor 440 comprises transducer to measure limb movements. FIG. 4 illustrates one possible combination of sensors that can be used. However, in other embodiments other types of sensors for measuring physiological data can be used and different combinations of sensors can be used. The data from these sensors can be used to collected data used by the DAU 210 in the concurrent measurement of signal data related to sleep architecture and of signal data related to sleep disruptions.

As described above, DAU 210 can include a wireless transmitter/receiver 377 incorporated into the data transfer module 326 to receive data from peripheral sensors (i.e., wireless ECG sensors, finger pulse oximeter, respiratory effort bands, sensors measuring leg movements, etc.) and/or transmit signals to an external computer system 390 for real time monitoring of the data being acquired by the DAU 210. Data acquired from these sensors can be used to determine the user's sleep architecture and/or to identify sleep disruptions that can negatively impact sleep quality.

According to an embodiment, each of these wireless sensor sub-systems can have a separate power supply and data storage. The DAU 210 and the wireless sensor sub-systems can be integrated to align the data from the sensor sub-systems with the data generated by the DAU 210. For example, the data can be aligned by using a common time stamp on all data that can be used to determine when data was recorded by the DAU 210 and/or the sensor sub-systems. According to an embodiment, this integration can be achieved by configuring the DAU 210 or one of the sensor sub-systems to operate to serve as a master device that wirelessly transmits a time stamp that is received by the other integrated components of the system. Each of the components of the system can include a wireless receiver for receiving the timestamp information and be configured to use the timestamp information transmitted by the master device to synchronize an internal clock to that of the master device or to use the timestamp information transmitted from the master device to timestamp data generated by the receiving device. According to an alternative embodiment, the sensor sub-systems can be integrated with the DAU 210 by coupling the DAU 210 to the sensor sub-systems using a wire. In such a wired configuration, the DAU 210 and the sensor sub-systems can operate using a common power supply and use common data storage.

In an embodiment, central sympathetic arousals or variability in sympathetic activation can be measured with two dry electrodes (i.e., capable of acquiring the ECG signal through clothes). One benefit of recording ECG is to more accurately identify cardiac problems (e.g., cardiac dysrhythmia, etc.). Alternatively, sympathetic arousals can be detected with a pulse signal or peripheral arterial tone signal. The pulse signal can be obtained using a sensor located at the user's forehead or any other location (e.g., ear, finger, etc.) which obtains capillary blood flow and is appropriate for either reflectance or transmittance methodologies/technology.

According to an embodiment, electro-neuro-cardio-respiratory sensors used to assess sleep quality can be incorporated into a single strip. FIG. 5 is an illustration of the integrated sensor strip 220 of FIGS. 2A and 2B used to acquire physiological signals according to an embodiment. As described above, the sensor strip 220 can be removeably coupled to the DAU 210 via a socket connection on the DAU 210 that electrically couples traces included in the sensor strip 220 with the DAU 210.

FIG. 5 is an illustration of an integrated sensor strip that can be used to acquire physiological signals that can be used in the concurrent measurements related to sleep architecture and sleep disruptions that is performed by the DAU 210 according to an embodiment. The integrated sensor strip can be used to implement sensor strip 220 associated with DAU 210 in FIG. 2. The sensor strip includes traces 510 that create electrical circuit connections while holding the sensors against the user's forehead. Within the sensor strip, EEG/EOG/EMG electrodes 520 are optimally positioned to measure rapid eye movements, cortical arousals, sleep spindles, K-complexes and stage sleep. One skilled in the art will recognize that sensors placed on the forehead are capable of acquiring both the brain's electrical activity and eye movements. In one embodiment, the strip provides for at least one sensor to be placed off the forehead in a non-frontal region of the brain to improve the detection of alpha waves which are used to assess sleep onset and cortical arousals. According to an embodiment, the sensor strip also provides the electrical pathway to drive the red and infrared light emitting diodes and photodiodes in the reflectance sensor 530. The reflectance sensor 530 can be used to generate signals for the calculation of oxyhemoglobin saturation and pulse rate of the user. From the reflectance sensor 530 inputs, a photoplethesmographic signal can be derived to measure respiratory effort via changes in forehead venous pressure.

In a preferred embodiment, the number of sensors included in the sensor strip is minimized and the connection between the sensors in the sensor strip and the DAU 210 is a wireless connection. As a result, the sensor strip can be configured for use on numerous sites, using various sensor combinations, and can be used with user's having different head sizes. In an embodiment, additional EEG sensors or connectors can be added to the strip to create the flexible interface to the electronic circuitry.

Furthermore, in some embodiments, inter-electrode spacing can be adjusted to accommodate adolescent and child head sizes. In some embodiments, sensor strap 230 can be integrated into or affixed over the sensor strip 220 to increase ease of preparation. Rather than using individual EEG sensors 520 and comfort strip 540, the sensor strip comprises a sheet of adhesive foam in which the sensors are embedded and with conductive gel placed over the conductive sensors. The use of foam or alternative potting method ensures the light from the reflectance sensor is transmitted into the skin and not directly to the photodiode.

Figure 6A:
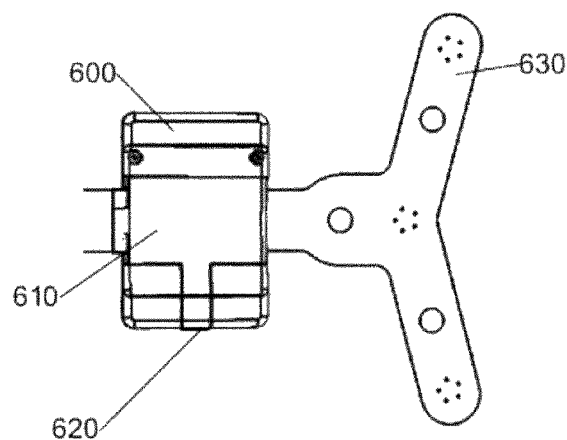
FIGS. 6A and 6B illustrate the data acquisition unit's enclosure and interface with the sensor strip according to an embodiment.
Figure 6B:
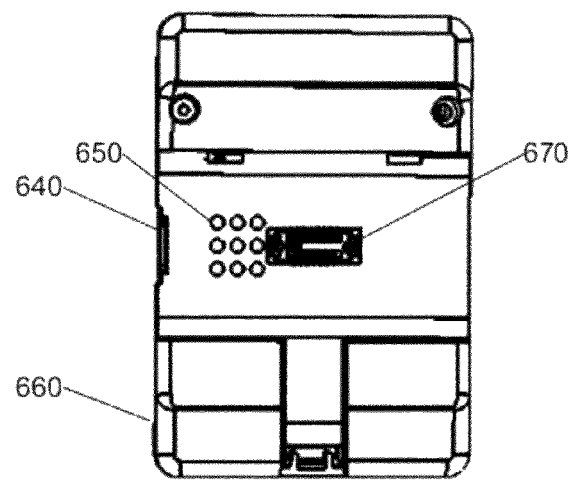

In a preferred embodiment the sensor strip 220 is detachable from the DAU 210. FIGS. 6A and 6B illustrate views of an enclosure of the DAU 210 and the interface with sensor strip 220 according to an embodiment. The DAU enclosure 600 includes a removable back cover 610 with a securing push tab 620 that holds the sensor strip 220 in place during use. Removal of the back cover exposes the micro-USB connector 640 and heat dissipating vent holes 650 which allow for data transfer and battery recharging. According to an embodiment, the connectors that allow the device to be connected to an external power source, such as AC power from the mains power, are not accessible when the system being worn by a user. In an embodiment, electrical pathways between the sensors and the electronics can be interfaced with one touch-proof connector for the ECG leads 660 and a connector in the center of the enclosure 670 for the sensor strip.

FIG. 2A illustrates a preferred method to measure airflow is by using a pneumotachometer mask 240 rather than the nasal cannula 250 that can be used in some embodiments (illustrated in FIG. 2B). FIGS. 7A, 7B, and 7C illustrate views of a disposable nasal mask 240 capable of measuring minute changes in airflow for use with DAU 210 according to an embodiment. According to an embodiment, the pneumotachometer mask 240 can be coupled to the DAU 210 and the pneumotachometer mask 240 can generate a signal that represents air flow through the user's nose. The DAU 210 can receive the signal and collect airflow data.

To accurately quantify airflow, a pneumotachometer-like interface 710 provides an air tight seal over and around the nose. A compromised seal can result in airflow leaking out the sides of the mask, thereby compromising the amplitude and accuracy of the measured airflow volume. Furthermore, too much pressure applied to a conforming material can cause discomfort and create hot spots which restrict blood flow and/or cause pressure sores. In an embodiment, to optimize the comfort and seal, a preferred embodiment includes an interface 730 made from injection molded silicone with thin dual wall cushion design that readily conforms to the patient's facial profile with minimal pressure. According to an embodiment, the interface 730 comprises thin walls around the edges of the mask that collapse in an anterior rather than posterior manner to conform to different facial characteristics. This approach allows less expensive injection molding techniques to be used to manufacture the disposable nasal mask.

In another embodiment, different thicknesses of material stiffen the region around where the tubes affix and bridging up to the nose so as to apply downward pressure against the outer walls to optimize the seal. In an embodiment, spacers 740 ensure the mask remains centered around the nares during use. In an embodiment, the ends of the tubes are positioned inside of the mask to optimize signal amplitude. In alternative embodiments, the mask is made with a single-wall cushion and from any material which provides the necessary seal and comfort. One skilled in the art will recognize that nasal masks of different sizes can be used to accommodate different head and nose shapes and sizes. In an embodiment, if a user is a predominant mouth breather during sleep, a full face interface can be used to quantify nasal plus oral airflow.

According to an embodiment, a differential between the pressure within the mask and outside of the mask is needed for the mask to act as a pneumotachometer. In a preferred embodiment, this differential pressure is created by holes 720 which impact tidal volume during inspiratory and expiratory breathing. In an embodiment, tubing is affixed to the interface at the differential pressure chamber 750 and interfaces with the DAU 210 which contains a nasal pressure transducer so airflow can be measured.

In an embodiment, the number and size of the holes is carefully controlled optimize the amplitude of the signal. This tuning should avoid any noticeable restriction in inspiratory and expiratory airflow. In the preferred embodiment, a single configuration as to the size and number of holes in the opening is utilized for all adults. In alternative embodiments, a means to change the pressure can be provided by any number of means that increases or decreases the volume of airflow through the opening, including but not limited to changing the size and number of holes, providing means to partially or fully block any number of the holes, and/or adding or removing a mesh screen behind the existing opening. According to some embodiments, a screen can be affixed to either within or on the outside of the mask to increase signal amplitude because the size of the holes that can be manufactured with injection molding techniques is limited. Furthermore, in alternative embodiments, different masks can be manufactured for use with the system that have appropriate size/ volume of openings determined by the patient's lung volume. Lung volume can be readily estimated based on the surface area of the patient's body using any number of published formulas that include but are not limited to height, weight and age.

According to an embodiment, the mask can incorporate a smaller opening in the pressure cover for masks to be used for children. The masks can be sized for the smaller head size of a child and adapted for the reduced airflow volume per minute of breathing of a child (in comparison to an average adult). In a preferred embodiment, the required features incorporated into a single use disposable mask minimize dead space in the mask to reduce the risk of rebreathing of expired $CO_2$. According to an embodiment, stabilizing features are incorporated inside the mask to reduce dead space to ensure the interface does not shift completely against the nares and restrict airflow.

The mask can be secured to the face of the user using various techniques. In some embodiments, a slip-tube over nasal cannula tubing and/or at least one self-adjusting strap can be used to secure the mask to the user's face. According to alternative embodiments, a different number of straps can be used and/or integration of the security of the system with alternative device(s). For example, more sophisticated means to easily increase or decrease the tension on the strap using a ladder lock, buckle or looping mechanism can be used. In one embodiment, a single strap circumvents the neck below the ears, while a second strap stabilizes the interface by affixing it to a device which includes a pressure transducer, which itself has a strap to secure it to the head. In an alternative embodiment, that can be used during laboratory polysomnography, a second strap circumvents the head above the ears. In another embodiment, a strap transverses the midline of the head and connects to a strap(s) which circumvents the head. In yet another embodiment, medical grade adhesive is used to tape the mask edges to the face.

Returning now to FIG. 1, FIG. 1 is a flow diagram of the method for assessing sleep quality according to an embodiment. The method can be used to assess the severity and impact of poor sleep quality. FIG. 1 can be implemented using the various systems described above in FIGS. 1-7.

The method begins with the acquisition of physiological signals from an adult or child at the DAU 210 (step 100). As described above, the data acquisition system performs concurrent measurements of two categories of signal data: (1) signal data related to sleep states, and (2) signal data related to the type of sleep disruption. In an embodiment, the apparatus used to acquire the physiological signals ideally uses electrodes and sensors, such as sensor strip 220, that can be self-applied with limited skin or scalp preparation, and which monitors signal quality during use and provides user feedback when signal quality problems are detected.

Once the physiological signals are obtained from the sensors, the signals are analyzed to assess the sleep stage of the user (step 110). As described above, according to some embodiments, the signal data from the sensors can be analyzed by the firmware included on DAU 210. In other embodiments, the data can be downloaded to external computer system 390 for processing and analysis. According to some embodiments, the DAU 210 can perform pre-processing on the data before the data is downloaded to the external computer system 390. According to an embodiment, the physiological signals acquired by the DAU 210 can be downloaded to external computer system 390 and stored in the patient data store 1332.

In an embodiment, various automated algorithms can be applied to the captured signal data. For example, in a preferred embodiment, the EEG signals are subjected to a filter bank that decomposes the signals into the frequency bands commonly used in the EEG analyses: eye movements/artifacts (<1 Hz), delta (1-3 Hz), theta (4-7 Hz), alpha (8-12 Hz), sigma (12-16 Hz), beta (18-30 Hz), EMG/artifacts (>32 Hz). Those skilled in the art will recognize that any other frequency band can also be used where advantageous. Those skilled in the art will also recognize that the filter bank can be realized with FIR filters, IIR filters, wavelets, or any other similar technique for time-frequency decomposition of signals.

In a preferred embodiment, REM sleep can be distinguished from non-REM sleep on the basis of ratios between beta EEG power (e.g., 18 to 32 Hz) and delta power (e.g., 1 to 3 Hz) within a pre-defined time window, or on the basis of a measure of agreement between the 2 EEG signals acquired simultaneously. The measures of agreement, when calculated over a short time window (e.g. 2-5 seconds) will behave markedly differently in case of eye movements than in case of delta waves (which can easily be confused with each other if only frequency analyses are used). According other embodiments, any statistical measure of agreement, such as Pearson's correlation coefficient or coherence, can be used for this purpose. Ratios of delta (e.g., 1 to 3.5 Hz) to beta (18-32 Hz) and theta (4-7 Hz) power are used to identify slow wave sleep.

In alternative embodiments, the detection of sleep stages can be performed using more sophisticated linear or non-linear mathematical models (e.g., discriminant function, neural network, etc.) with variables that can be obtained from the EEG, EOG and ECG signals. Short duration fast-frequency EEG bursts are measured using one-second measures of power spectra to detect sleep spindles (that only appear during Stage 2 sleep) and EEG arousals (that appear in Stage 1 sleep). The distinction between the spindles and arousals can be made on the basis of their duration (spindles are shorter, arousals longer than 3 seconds). One skilled in the art will recognize that in addition to the techniques mentioned above, ratios of the power in various frequency bands, or linear combinations (weighted sums) of the power in various frequency bands can be used for separation of sleep states and waveforms. In addition to power spectra analysis of the EEG, one skilled in the art will recognize that variability in the ECG signal increases during rapid eye movement sleep. These patterns are different from the rapid bradycardia-tachycardia changes that occur as a result of an arousal or with the sinus arrhythmia that can be seen in children. In an embodiment, full-disclosure recording are optionally presented to allow the signals and automated sleep staging to be manually viewed and edited using a user interface provided by the data processing and visualization module of the external computer system 390. Standard sleep architecture parameters are then computed, including total sleep, REM and SWS times, sleep, REM and SWS latency, and sleep efficiency. Mean power spectra analysis computed across stage N1, N2, N3 (SWS) and REM states in the delta, theta and alpha ranges can be used to identify abnormal characteristics associated with abnormal sleep characteristics.

Once the signals have been analyzed to assess the sleep stage, the signals can be analyzed to identify patterns of sleep and breathing discontinuity (step 120). As described above, the data acquisition system collects and records data related to sleep disturbances concurrently with data related to sleep architecture. The sleep disturbance data is analyzed to identify patterns of sleep and breathing discontinuity. As described above, according to some embodiments, the signal data from the sensors can be analyzed by the firmware included on DAU 210. In other embodiments, the data can be downloaded to external computer system 390 for processing and analysis. According to some embodiments, the DAU 210 can also perform some pre-processing on the data before the data is downloaded to the external computer system 390 for analysis.

Sleep medicine practice parameters define standards for the assessment of sleep and breathing discontinuity. An apnea is defined as a 10-second cessation in airflow. A hypopnea requires a change in airflow with an accompanying cortical arousal, or oxyhemoglobin desaturation. According to an embodiment, event scoring can be performed by marking breathing discontinuity events in a record and then tallying the events and dividing by total sleep time. In a preferred embodiment, more sophisticated algorithms are applied to the acquired signals to detect and quantify sleep disordered breathing in ways that are not possible with visual scoring. Various algorithms that can be used in embodiments are described below. These algorithms expand upon the rudimentary approaches used for visual scoring and can provide improved measures of sleep disruption and disordered breathing severity that will contribute to improved differential diagnoses or estimated risk for chronic diseases.

Changes in tidal volume can occur as a result of ventilation or central breathing instability vs. airway obstruction. The sleep stage or medical conditions which contribute to these different types of breathing is important because selecting the appropriate therapy is dependent distinguishing these differences. Flow limitation only occurs when the airway is partially obstructed and manifests as a flattening in the inspiration peak of the airflow signal. An example of flow limitation is provided in FIG. 7. Thus the presence of at least one flow limited breath during a hypopnea is used to confirm that an abnormal breathing event has an obstructive element. When a tidal volume change is detected in the absence of flow limitation, the event is characterized as a central or mixed event.

In a preferred embodiment, flow limitation is detected by comparing the shape of the airflow using two reference airflow shapes, with one shape representing a breath with no obstruction and the other shape reflecting a flow limited breath. There are a number of techniques which can be used to compare signal shapes, including, but not limited to, neural network and cross correlation analyses, etc. Alternative embodiments can use as few as one or multiple reference signals for the detection of flow limitation. The accuracy of flow limitation/obstructive breathing detection can be improved when patterns across previous and subsequent breaths are compared and combined with the recognition of significant changes in tidal volume (i.e., apneas). The detection of flow limitation can be improved when signals are normalized to periods of persistent loud snoring. In an embodiment, the inability to recognize an airflow signal in at least two breaths is an entry point for differentiating apnea from a hypopnea. The pattern of distinct inspiratory peaks coupled with a decrescendo/crescendo change in tidal volume and absence of flow limitation is used to characterize central events.

Flow limitation can persist for long extended periods of sleep independent of discrete apneas and hypopneas and thus its prevalence throughout the night is quantified. In an embodiment, two minute periods of flow limitation are classified as an equivalent to an apnea or hypopnea events in the calculation of a sleep disordered breathing/obstructive index. This obstructive index has been shown to increase the correlation between abnormal nocturnal breathing and daytime impairment (i.e., slower reaction times). In an embodiment, the percentage of the night with flow limitation, stratified by position and/or snoring level can also be measured and reported to improve the quantification of sleep disordered breathing severity.

When the pneumotachomter nasal mask 240 is properly worn, the amplitude of the acquired airflow signal is directly proportional to the change in airflow volume during sleep. In other words, this system can provide a more accurate measure of subtle changes in airway obstruction than any conventional approach. This improvement provides a measurement of each breath in units which apply consistently across individuals and allow for a quantified measure of obstructive breathing (e.g., hypopnea associated with 20 milliliters per second changes in airflow). This improved precision allows for the assessment of flow limitation to extend beyond a temporal measure (i.e., appearance based on the flow shape) to assess the relationship between tidal volume and flow limitation. The inventors argue that reductions in tidal volume or minute ventilation resulting from partial or full obstruction provides a more sensitive correlate with the symptoms associated with sleep disordered breathing (e.g., drowsiness, hypertension, etc.).

In a preferred embodiment an acoustic microphone can be used to acquire quantitative snoring (e.g., measured in decibels) in order to obtain the most accurate information related to the snoring patterns or changes in snoring patterns associated with OSA and/or treatment outcomes. These snoring pattern changes are used as behavioral arousal indicators to independently confirm that changes in airflow are a result of sleep disordered breathing (see FIG. 8). During apnea events, snoring will stop as a result of the absence of breathing. During hypopnea events, snoring amplitudes increase as a result of the partial collapse of the airway. Loud steady snoring commonly coincides with periods of flow limitation. Crescendo and decrescendo patterns at the apex of changing airflow pattern are used to confirm patterns associated with central sleep apnea. When a patient is not a loud snorer, the behavioral indication of an arousal will be the appearance of a short snore at the termination of a hypopnea.

Figure 8:
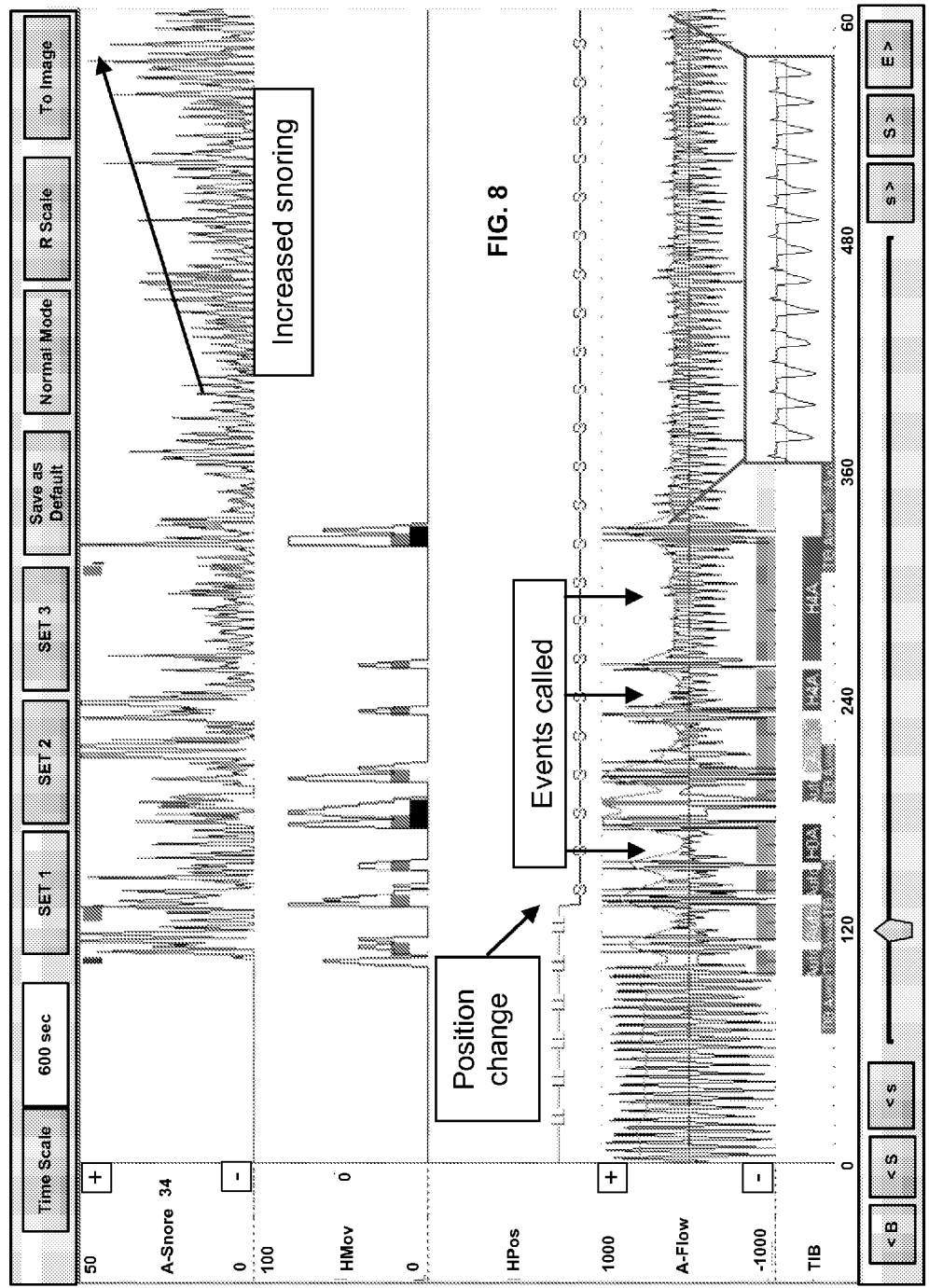
FIG. 8 includes example data illustrating changes in patterns of physiological signals which define behavioral measures of sleep/wake and the impact of position on sleep disordered breathing patterns as a result of position change according to an embodiment.

FIG. 8 illustrates example data captured by the sensors and the DAU 210 and downloaded to a computer system. According to an embodiment, this data can be displayed using a user interface generated by the data processing and visualization module of external computer system 390. In the embodiment, the user interface illustrates the level of detail of information that can be captured using the system and how the data can be displayed. In the data illustrated in FIG. 8, the user changed position from a lateral left position to a supine position. This change of position results in a drop in flow volume of 50%, constant flow limitation, and a steady increase in snoring. The movements that occur immediately after the position change resulted in a number of epochs being identified as "awake." However, only three of the detected events are accepted in the calculation of the severity of sleep disordered breathing.

In an embodiment, acquiring the snoring/breathing signal with an acoustic microphone at a minimum of two kilohertz allows this signal to be analyzed in the frequency domain to detect and quantify environmental noise or a snoring bed partner. In an embodiment, temporal and frequency analysis of this high fidelity signal using wavelets or similar type analysis allows snoring to be differentiated from coughing or wheezing. In one embodiment, because snoring represents the most subtle form of sleep disordered breathing and is considered by some to be an independent risk factor for carotid artery atherosclerosis, the high fidelity signal is combined with the detection of flow limitation to improve on the prediction of the onset of this medical condition. One skilled in the art recognizes the opportunities to combine voice quality pattern recognition with changes in actigraphy, airflow, and oximetry to further differentiate abnormal respiration. Detection of coughing, wheezing and similar respiratory breathing patterns are useful in providing a differential diagnosis between OSA and asthma or chronic obstructive pulmonary disease or a lack of response or use of steroid inhalers.

According to an embodiment, to improve detection accuracy of obstructive breathing related snoring changes, the signal is optimally transformed using integration or other signal processing routines to accentuate and consolidate the sound change. As an alternative to an acoustic microphone, snoring can be detected from any number of means, including measurement of vibration changes, or detection of high-frequency (>70 Hz) bursts in the airflow signal. In a preferred embodiment, signals from the microphone are aligned with the breathing from the airflow signal to ensure noise due to movement or the environment is not characterized as snoring. When the snoring signal is consolidated/transformed in this manner described previously, the snoring signal must be phase shifted to account for the snoring amplitude extending beyond the negative value associated with the expiration in the airflow signal. When snoring is analyzed in this manner, its presence can be used as a behavioral measure of sleep (in the absence of neuro-physiological measures).

Figure 9:
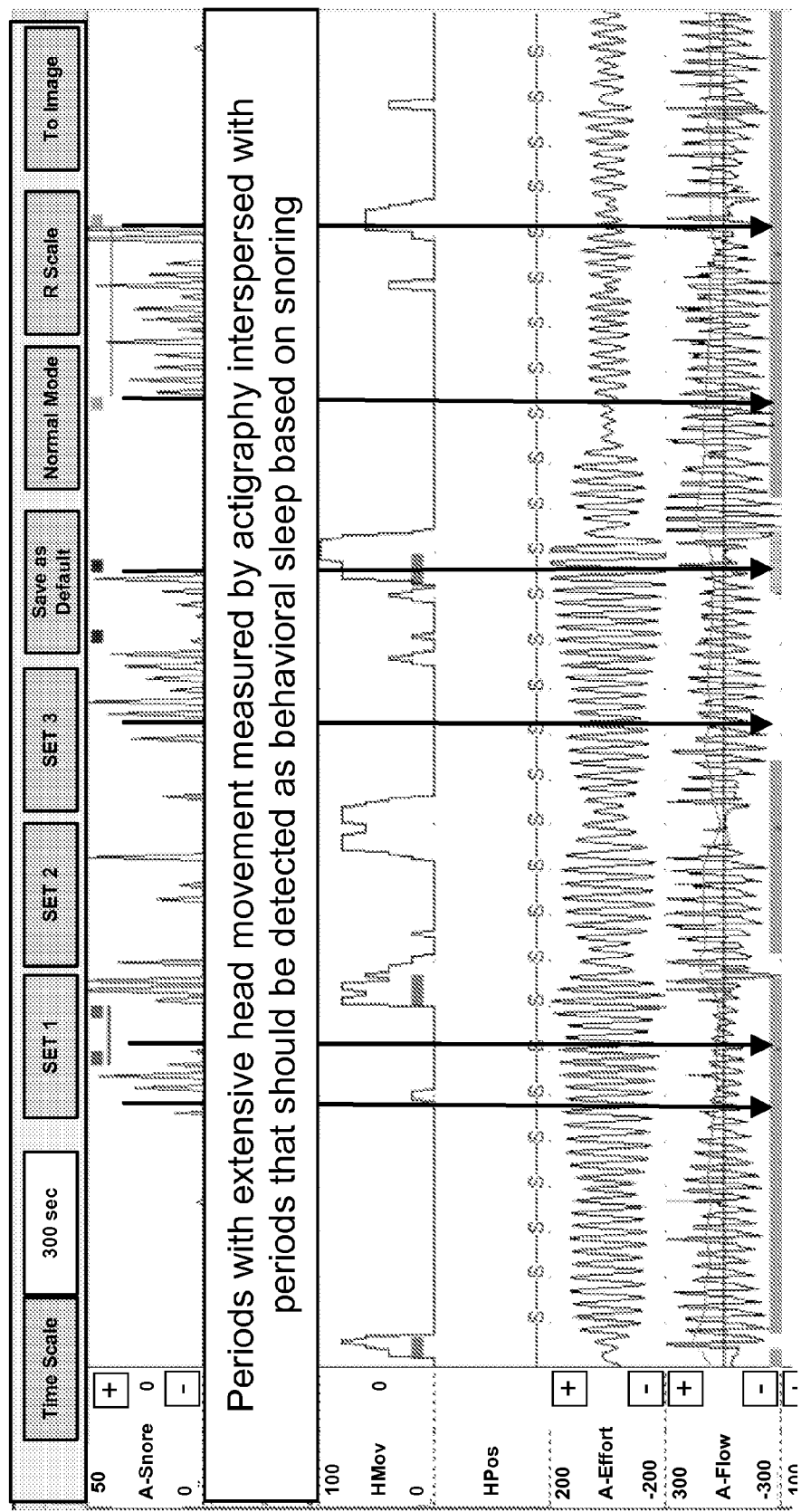
FIG. 9 includes example data illustrating how actigraphic measures of movement can be confirmed with snoring patterns to recognize behavioral sleep/wake patterns according to an embodiment.
Figure 10:
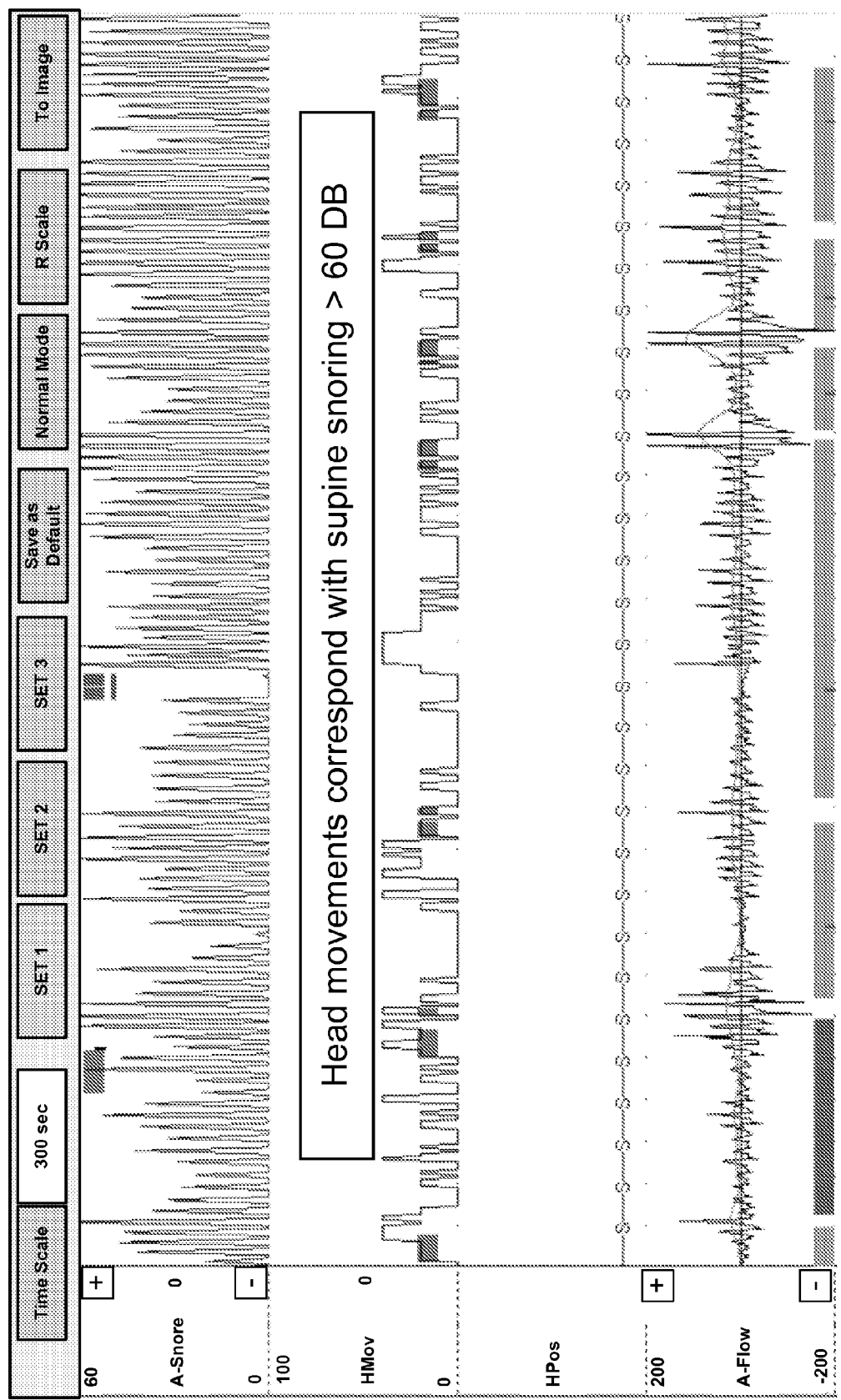
FIG. 10 includes example data illustrating how the capability of actigraphy to measure increased breathing effort associated with loud snoring according to an embodiment.

From the actigraphy, long duration or high intensity head or body movements are used to identify periods likely contaminated with signal artifact (see FIGS. 9 and 10). The duration and frequency of head or body movements are also useful in differentiating behavioral sleep from wake. FIG. 9 includes example data that displays periods with substantial head movement (HMOV) indicates the patient is awake. According to an embodiment, this data can be displayed using a user interface generated by the data processing and visualization module of external computer system 390. Actigraphy is so sensitive it picks up subtle respiratory-related movements. This pattern can be obtained with accelerometers mounted in the DAU or affixed to clothing or a belt worn in place of conventional respiratory effort belts. FIG. 9 illustrates an example of identification of periods for that could be incorrectly detected as being "awake" periods based on the HMOV, but should instead be detected as behavioral sleep based on the snoring signals.

Figure 11:
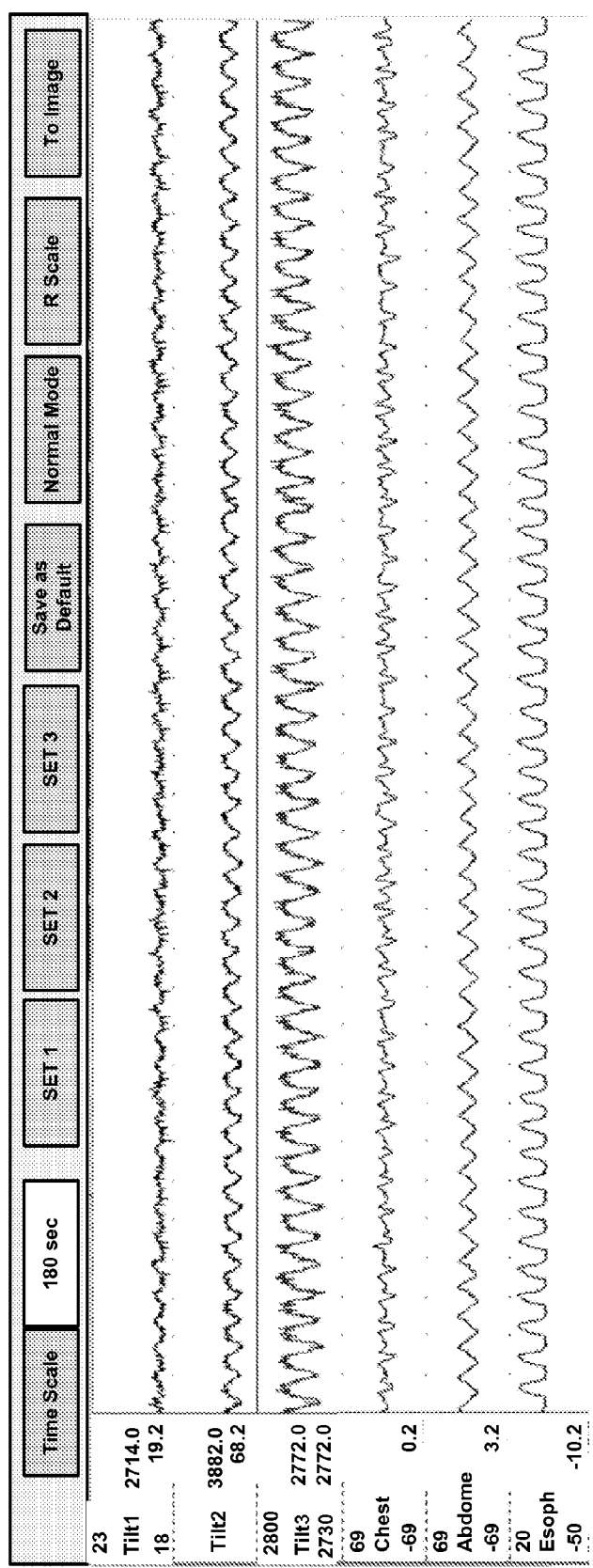
FIG. 11 includes example data comparing respiration information provided with actigraphy compared to conventional measures of respiratory effort according to an embodiment.

FIG. 10 illustrates example data that shows the influence of increased respiratory effort/snoring on the head movement signal. According to an embodiment, this data can be displayed using a user interface generated by the data processing and visualization module of external computer system 390. FIG. 10 illustrates that some periods could be incorrectly classified as "awake" periods based on head movements reflecting an increased effort to breathe. FIG. 11 shows surrogate measure of respiratory effort derived from the X, Y, and Z actigraphy channels (tilt 1, 2, and 3 respectively) compared to respiratory effort obtained from chest wall and abdomen effort belts and an esophageal balloon. FIG. 11 includes data that shows an example of respiratory effort obtained from the tri-directional signals obtained with actigraphy (e.g., Tilt 1, Tilt 2, and Tilt 3), compared with to respiratory effort obtained with chest and abdomen belts and esophageal balloon. According to an embodiment, this data can be displayed using a user interface generated by the data processing and visualization module of external computer system 390. In a preferred embodiment, the actigraphy signal is filtered to isolate signals associated with breathing and respiratory effort to remove these from the head movement signal. Simple filtering techniques timed to the frequency of the breathing is sufficient to isolate the effort signal as well as remove it from the head movement signal. Alternatively, adaptive filtering is employed to reduce harmonics caused by applying the incorrect band-pass filters. The resulting movement measure shows only gross/important changes. The resulting surrogate respiratory effort signal (when combined with the airflow signal) provides for improved differentiation between obstructive and central breathing events.

Figure 12:
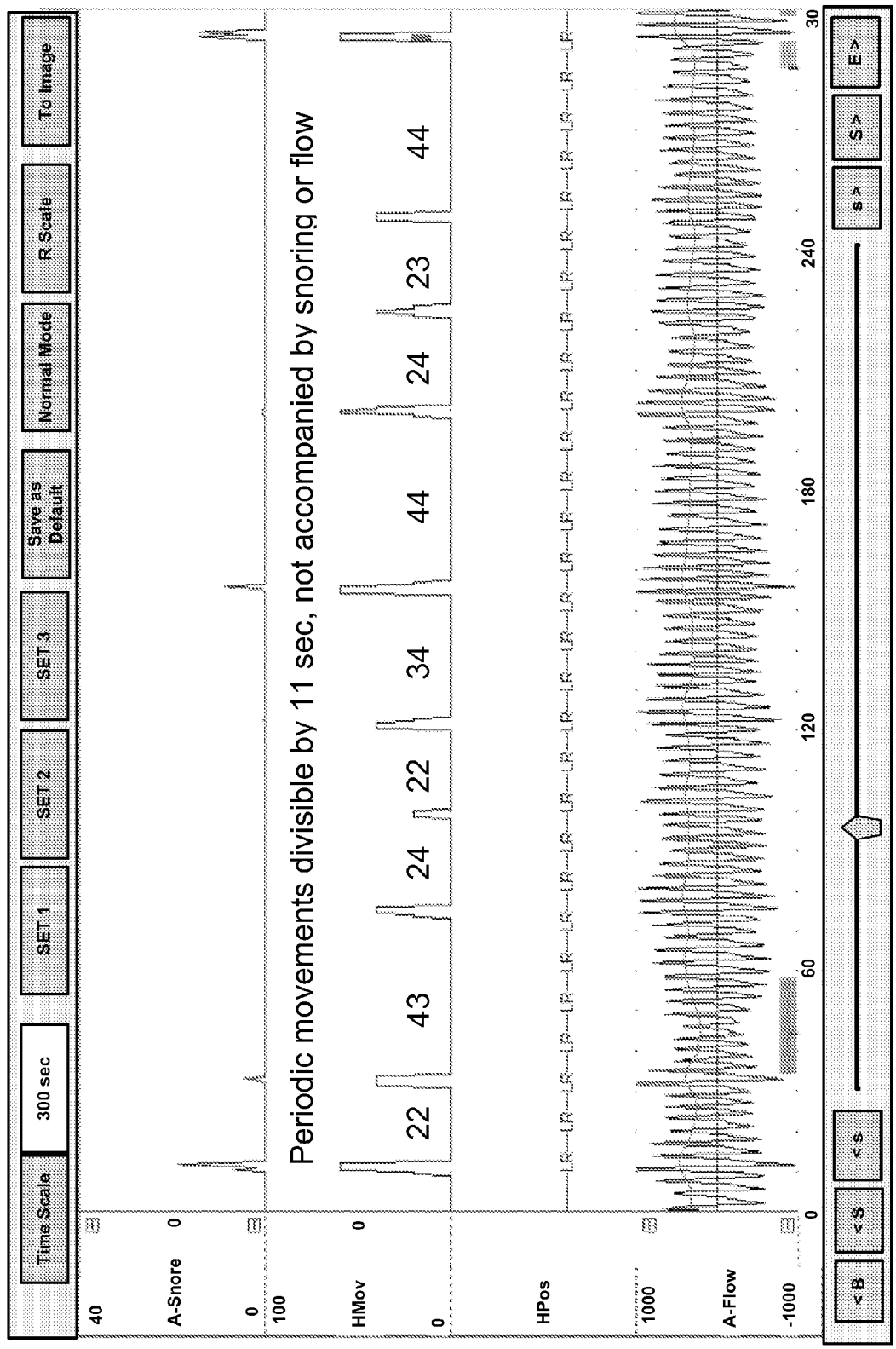
FIG. 12 includes example data that presents patterns associated with periodic limb movements that could be detected with actigraphy.

In an embodiment, the actigraphy signal can be used to detect periodic limb or body movements as shown in FIG. 12. According to an embodiment, this data can be displayed using a user interface generated by the data processing and visualization module of external computer system 390. Periodic limb movements appear in the actigraphic signals acquired on the head as movements of short duration and high intensity that occur at regular intervals with no apneas or hypopneas in the airflow signal. In one embodiment, accelerometers could be placed on the ankles as a separate adjunct device that directly measures leg movements and transmits this information wirelessly to the main device. Because arousal from either sleep disordered breathing or periodic limb movements contribute to sleep fragmentation and daytime somnolence, the frequency, intensity and duration of head movements during time in bed can be used to independently quantify the quality of sleep. These measures of sleep quality can be especially useful for use in diagnosing sleep quality children, because cortical arousals are more difficult to measure and disrupted sleep causes daytime drowsiness, a symptom that affects those with childhood OSA and attention deficit/hyperactivity disorders.

As described previously, the actigraphy signals can be used independently to distinguish sleep from wake, and/or combined with changes in snoring and/or airflow to further improve the accuracy of sleep/wake detection. FIG. 9 highlights temporal periods of snoring between periods of gross head movement, with snoring indicating the patient is asleep and the head movement indicating the patient is awake. In the preferred embodiment, sleep and wake are determined independently for movement and snoring, and algorithms are applied to improve the accurate detection of behavioral sleep and wake when the results from the independent measures conflict. These rules require the accurate detection of snoring and timing of snoring with airflow to ensure that environmental noise is not contributing to the misclassification of sleep. Returning now to FIG. 1, once behavioral sleep/wake is determined, epoch classifications can be compared to classifications previously made by neurophysiological means (see step 110 of FIG. 1) to improve the overall accuracy of the sleep/wake classifications.

Arousals which disrupt sleep continuity can be distinguished from any number of signal patterns and preferably multiple signals are used to confirm the veracity of the arousal. For example, sleep spindles and arousals have a similar frequency domain characteristic, and it may be difficult to distinguish spindles from short arousals. Sleep spindles indicate the patient is in N2 sleep and the absence of behavioral arousals would be expected. Cortical arousals are expected to be accompanied by changes in heart rate, head movement, respiration, blood flow or any number of physiological markers. The temporal alignment of arousals from multiple sources can be performed within an arousal window that accommodates physiological phase delays (e.g., circulation delay causes four-second latency in pulse rate). The measurement of non-abating sympathetic hyperactivity and its impact on autonomic nervous system dysfunction and sleep continuity/quality can be achieved with a frequency domain analysis of the heart rate variability (using either ECG or pulse rate).

Once the signals have been analyzed patterns of sleep and breathing discontinuity, the sleep architecture for the user, as well as the respiration and fragmentation patterns for the user can be summarized (step 130). As described above, according to some embodiments, the signal data from the sensors can be analyzed by the firmware included on DAU 210. In other embodiments, the data can be downloaded to external computer system 390 for processing and analysis. According to some embodiments, the DAU 210 can perform pre-processing on the data before the data is downloaded to the external computer system 390.

In an embodiment, the number of events per hour derived from each of the neuro-cardio-respiratory measures are measured separately and subsequently combined to profile the level of sleep disruption or sleep continuity. The frequency and duration of menopausal hot flashes can also be measured and temporally associated with sleep stage and arousal. In a preferred embodiment, hot flash related sympathetic arousals are measured directly by electrocardiogram, pulse oximetry, or peripheral arterial tone, however, indirect measures such as the electrical conductivity of the skin (galvanic skin reaction, "GSR") can be alternatively used. In the preferred embodiment, the sleep studies are conducted over multiple nights with a report providing night-to-night comparisons of each of the measures described previously to better profile variability in sleep architecture and continuity.

A number of biological markers can also be optionally obtained to increase diagnostic accuracy, the predicted likelihood of disease onset, or to guide treatment (step 140). The biological marker results can be derived from any number of sample means including blood, saliva, serum, urine, hair, etc. that are sensitive to a particular disease phenotype. For example, the result from a glucose tolerance test can be combined with the amount of slow wave sleep to assess the risk of Type II diabetes. Similarly test results for inflammatory markers such as C-reactive protein assays, Interleukin-6 (IL-6) or other pro-inflammatory cytokine can be similarly combined with sleep measures, e.g., amount of slow wave sleep, total sleep time, amount of REM sleep, or sleep continuity disrupted by repeated sympathetic arousals, to determine the likelihood of an individual having or developing cardiovascular disease, hypertension, chronic fatigue syndrome, fibromyalgia, depression, and autoimmune disorders metabolic X syndrome.

In a preferred embodiment, the information obtained from the detection of sleep quality is combined with questionnaire responses to improve diagnostic capabilities of the system (step 150). The questionnaires can identify subjective measures of insomnia, depression, mood, anxiety, sleepiness and/or other factors that can impact sleep quality. According to some embodiments, the questionnaires can be implemented on a web portal and the user is presented with a web page or series of web pages that present the questionnaire to the user and capture the user's response. According to an alternative embodiment, the questionnaires can be implemented using client-server software on the external computer system 390 that presents the user with a user interface that displays the questionnaire, captures the user's responses, and stores the responses on a memory devices such as a SD card and/or transmits the responses to a doctor or clinician for use in analyzing the sleep quality of the patient using the DAU. According to an embodiment, the questionnaire responses can be stored in the patient data store 1332. The questionnaire responses can then be correlated with detection of sleep quality described above to identify factors that may be negatively impacting sleep quality.

For example, if a patient had a high pre-test probability of having OSA but little to no sleep disordered breathing was detected, a report can include a suggestion that the patient be referred to an expert for a consultation. A system which includes information derived from analytical techniques that utilize nocturnal measures of sleep disordered breathing in combination with clinical, history and physical information is especially useful in children. Because there is a significant overlap in the symptoms related to attention deficit/hyperactivity disorders (ADHD), obstructive sleep apnea (OSA) and asthma, the capability of a clinician to obtain an accurate differential diagnosis is improved if the probabilities of a patient having each of the diseases is provided. In an embodiment, the study report can incorporate information derived from questionnaire responses that combine demographic (i.e., age, gender, etc.), anthropomorphic (i.e., height, weight, body mass index, neck, stomach or hip circumference, etc.), history of diseases, and abnormal self-reported levels of depression, mood, anxiety, and sleepiness. These responses can be obtained from any number of conventional questionnaire instruments (e.g., Epworth Sleepiness Score, Beck Depression Index, State-Trait Anxiety Index, Pittsburgh Insomnia Rating Scale, Profile of Mood states, etc.) or any combination of questions that provide the appropriate information. In a preferred embodiment a limited number of questionnaire responses can be selected and combined with the sleep quality measures to develop a patient profile.

Abnormal psychophysiological conditions are then identified in some embodiments (step 160). In an embodiment, sleep quality is associated with its impact on daytime psychophysiological states or conditions, e.g., somnolence, mood and memory. This association can be obtained from any number of conventional neuropsychological assessments, including but not limited to computerized behavioral tests, continuous performance tests or psychomotor vigilance tests, neurocognitive factors change or similar means with or without the acquisition of physiological signals (i.e., EEG, ECG, etc.). Conversely, systems designed for objective assessment of daytime psychophysiological states or conditions will include sleep architecture and continuity measures derived from the described system.

To improve the diagnostic accuracy of the sleep study results, the individual's data can be additionally compared to a database of values from healthy individuals and/or patients with chronic diseases (step 170). According to an embodiment, the database of values from healthy individuals and/or individuals with chronic diseases can be stored in comparative data data store 1338, and the data from the comparative data data store 1338 can be compared to the individual user's data by executing comparison algorithms on external computer system 390. This methodology can be applied to the data to calculate odds ratios or probability estimates as to the likelihood an asymptomatic individual may be developing a chronic disease that can negatively impact sleep quality (e.g., Type II diabetes, hypertension, etc.). Questionnaire responses obtained can be used to establish a pre-test probability of an individual need for a sleep study. Alternatively, the results obtained prior and subsequent to a treatment intervention can allow the change in risk level based on the treatment efficacy to be determined and reported. One skilled in the art will recognize that any number of statistical procedures are appropriate for assigning a pretest probability or odds ratio including but not limited to logistical regression analysis, etc.

A study results report can then be generated that integrates the findings from the steps described above with disease management recommendations (step 180). According to an embodiment, the disease management recommendations can be stored in disease management recommendations data store 1336 and the external computer system 390 can execute a comparison algorithm to identify which disease recommendations are appropriate for the for the individual user for whom the study results report is generated. In an embodiment, the disease management recommendations can be selected based on the results of the analysis of the signal data obtained by the DAU 210 and other physiological and psychopyshiological data obtained using one or more of the techniques described above. For example, if the user has been identified to have hypertension, recommendations for treating hypertension can be provided in the sleep study report. These recommendations can be used by the user and/or a treating physician to manage conditions that can have a negative impact on sleep quality.

In an embodiment, the study results report can be stored in the reporting data store 1334. According to an embodiment, the external computer system includes a user interface module for displaying the report data. In some embodiments, where the external computer system is implemented as a web portal, a web page or series of web pages can be provided that allow patients and/or clinicians to generate and view reports.

The sleep study metrics obtained from this system can provide the basis for report recommendations that are used to assist clinicians and patients in the management of chronic diseases. For insomnia patients, the sleep assessment study allows one to determine the severity of the sleep disturbances and identify insomnia attributed to physical causes which result in repeated sympathetic arousals (e.g., hot flashes, periodic limb movements, etc.). Alternatively, when insomnia appears to be caused by psychological problems (i.e., acute stress, depression, anxiety) it should be addressed with relaxation techniques, changes in diet and exercise, improved sleep hygiene (i.e., regular sleep routine) and counseling to help resolve the psychological problems. If hypnotics, anxiolytics, or other medications are prescribed, a repeat sleep study is recommended to assess changes in sleep architecture resulting from use or discontinued use of the medication(s).

The biomarker of early onset REM sleep and increased REM density and duration can be used to objectively confirm major depression, independent of clinical impressions or self-reported mood depression scores. These markers can also predict successful treatment outcomes and differentiate/identify those who have mood disorders related to insomnia. A repeat sleep study after prescription of Selective Serotonin Reuptake Inhibitors (SSRI) medications can assess treatment outcomes by determining if there has been changed or normalized consolidation and reduction in REM density and duration. For a patient with menopausal symptoms, the relationship between the frequency and duration of hot flashes, sleep stage and sleep continuity and the temporal association of sympathetic arousals and hot flashes can be objectively determined. If it is determined that the duration of REM sleep increases the sympathetic arousal and results in periodic sleep state insomnia, then treatments which reduce REM sleep can be recommended. Repeated measure testing is appropriate for the treatment of any medical condition that includes the need to reduce the latency or amount of REM sleep. Treatment to reduce REM sleep is not limited to pharmacological means, and includes feedback or other methods that shift sleep stage from REM to non-REM sleep (e.g., auto or vibrotactile feedback). Repeat testing can also confirm that appropriate or normal amounts of SWS are obtained to reduce the risk of obesity and insulin resistance or to assess the benefit non-hormonal treatment interventions.

Sleep architecture and continuity study results can be combined with a blood glucose tolerance assay are used to fully diagnose borderline Type II diabetes cases and recommend early management and monitoring. Measures of SWS and delta activity across sleep stages will be used to determine if abnormal sleep architecture or patterns are contributing to insulin resistance. If the results indicate that the patient has a sleep disorder recommendations for an appropriate study can be made. If sleep disorder is found, then treatment for the disorder can be recommended before, or in conjunction with treatment or preventative measures taken for the diabetes. If risk of Type II diabetes is indicated, then behavioral intervention to improve sleep hygiene and duration can be advised in addition to regular exercise and other preventative measures. If diabetes has developed and no indication of a concurrent sleep disorder is indicated, then sleep studies can be recommended or used to monitor treatment and to ensure that a sleep disorder (such as OSA) does not develop.

Disturbed sleep with abnormal sympathetic arousals in conjunction with immune markers (e.g., C-reactive protein assays, Interleukin-6 (IL-6) or other pro-inflammatory cytokine measures) can be used to determine early risk for development of cardiovascular disease or confirm inflammation associated with fibromyalgia, chronic fatigue, or similar diseases.

Measures of total sleep time, the amount of SWS, and sleep fragmentation independently or in combination with measures of between leptin and ghrelin can be used to assess the potential for sleep quality contributing to the consumption of high carbohydrate foods in obese patients. Repeated testing provides objective assessment of improvements in total sleep time and SWS as part of a dietary and exercise intervention.

In a preferred embodiment, the novel measures obtained from the airflow and actigraphy signals and described previously can be incorporated into the report to improve its clinical and diagnostic value. For example, the breathing frequency during sleep can be averaged and compared to normative values to identify breathing abnormalities. Quantifying the variability of the non-flow limited breathing amplitude and snoring and relating this variability by sleep position can provide unique information related to subtle disease states. The frequency, intensity and duration of head movements during time in bed can be used to independently quantify the quality of sleep which is especially relevant because children with OSA, ADHD and disturbed sleep from other causes all have daytime drowsiness. Thus, reporting sleep quality can be used to differentiate children who have disturbed sleep from other causes from those with sleep disordered breathing. Quantification techniques for the described measures include linear, Gaussian based approaches as well as non-linear mathematical applications applied to the entire study or segments of the study.

In a preferred embodiment this system is deployed using a web-based portal, such as the remote server described above. This approach eliminates the problems associated with operating desk top software within a local area network designed to control confidential patient information. The web-portal is designed to upload recording from the DAU and questionnaire responses prior to applying the analytical software. The recordings and questionnaire responses can be uploaded independently and/or to the portal via a mobile device, electronic medical records system or from a desk top computer. The web-portal provides clinicians the means to host inspection of the full disclosure recording and/or review and download of the study report.

One skilled in the art will recognize that the described system can be configured for multi-modality approaches to assess sleep quality. Table 1 provides a plethora of exemplary system combinations which are dependent on the needs of the user (e.g., ease of use, size, power requirements, cost, physiological information needed) to diagnose a disorder/disease or assess treatment outcomes as a result of an intervention. Option 1, for example, provides the simplest configuration to assess changes in sleep disordered breathing as a result of a treatment intervention such as an oral or Provent™ appliance. Options 2 through 5 provide greater precision as to the measurement of respiratory related arousals on sleep quality. Options 6 and 7 are equivalent to and could be used as a replacement for the current method used to obtain laboratory polysomnography. If a clinician suspects the patient has depression but hasn't ruled out OSA, then options 8 through 10 can provide the needed information. If OSA has been ruled out as a possible diagnoses, then option 11 is the simplest approach to assess changes in sleep architecture and sleep continuity as a result of interventions for menopausal hot flashes or depression-like REM patterns, etc. Options 12 through 14 can provide more thorough assessments of physiology impacted by poor sleep quality.

According to an embodiment, where oximetry is not required, the size of the DAU 210 allows the DAU to be readily mounted on the user's forehead. When the DAU is located on the forehead it can be more difficult to acquire more than one channel of EEG/EOG needed to accurately assess sleep architecture. When options 1 through 5 are implemented with the DAU above the forehead, the system can be used to assess treatment outcomes when worn simultaneously with continuous positive airway pressure (CPAP). In an embodiment, the pressure/flow signal derived from the CPAP tube can be directly input to the DAU 210 so long as the nasal pressure transducer can measure +/−10 inches/H20. In an alternative embodiment, a pitot tube can be placed in-line between the CPAP tube and mask to extract the airflow signal for input into the high resolution DAU nasal pressure transducer (i.e., +/−1 inch/H20).

One skilled in the art will recognize that the options provided below are non-inclusive of all possible combinations which can be achieved with the system described above. Given the flexible deployment of the sensor/signal sets, steps 140 through 180 in FIG. 1 remain part of the system, it simply affects the amount of information that can be obtained when compared to a database of data with similar measures.

TABLE 1

Sensor, Signal and Analyses Combinations to Quantify Sleep Quality

| | Airflow-mask, cannula | Behavioral-Arousals, sleep/wake | Sleep architecture, arousals | Oxygen saturation | Cardiac-patterns, arousals | Acoustic-breathing, snoring | Respiratory effort | Limb Movement detection | Location of DAU |
|---|---|---|---|---|---|---|---|---|---|
| 1 | Yes | Yes | | | Yes | | | | Forehead |
| 2 | Yes | Yes | | | | Yes | | | Forehead |
| 3 | Yes | Yes | | | Yes | | Yes | | Forehead |
| 4 | Yes | Yes | | | Yes | Yes | | | Forehead |
| 5 | | Yes | | | Yes | Yes | Yes | | Forehead |
| 6 | Yes | Yes | Yes | Yes | Yes | Yes | Yes | | Head |
| 7 | Yes | Yes | Yes | Yes | Yes | Yes | Yes | Yes | Head |
| 8 | Yes | | Yes | | Yes | | | | Head |
| 9 | Yes | | Yes | | Yes | | | | Head |
| 10 | Yes | | Yes | Yes | Yes | | Yes | | Head |
| 11 | | | Yes | | Yes | | | | Head |
| 12 | | | Yes | | Yes | Yes | | | Head |
| 13 | | | Yes | | Yes | Yes | Yes | | Head |
| 14 | | | Yes | | Yes | Yes | Yes | Yes | Head |

Those of skill in the art will appreciate that the various illustrative modules and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules and method steps described in connection with the embodiments disclosed herein can be implemented or performed with hardware such as a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor is hardware and can be a microprocessor, but in the alternative, the processor can be any hardware processor or controller, microcontroller. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in computer or controller accessible on computer-readable storage media including RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the invention and are therefore representative of the subject matter which is broadly contemplated by the present invention. It is further understood that the scope of the present invention fully encompasses other embodiments and that the scope of the present invention is accordingly limited by nothing other than the appended claims.

The invention claimed is:

1. A system for assessing sleep quality of a user, the system comprising:
    a sensor strip comprising at least one sensor, which detects data indicative of normal and abnormal patterns during sleep of a user, and a tab comprising traces electrically coupled to the at least one sensor, wherein the sensor strip is configured to be positioned on the user's forehead and removably coupled to at least one strap;
    a data acquisition unit comprising an enclosure having a connector therein, wherein the data acquisition unit is configured to be positioned on the user's head, wherein the tab of the sensor strip fits within the enclosure and is detachably coupled to the data acquisition unit within the enclosure such that the traces of the tab are electrically coupled to the data acquisition unit via the connector, and wherein the data acquisition unit collects the data indicative of normal and abnormal patterns during sleep from the at least one sensor in the sensor strip.

2. The system of claim 1 further comprising a nasal pneumotachometer in communication with the data acquisition unit to provide the data acquisition unit with a signal indicative of airflow through the user's nose, the pneumotachometer being capable of detecting minute changes in airflow through the user's nose.

3. The system of claim 1 further comprising a nasal cannula in communication with the data acquisition unit to provide the data acquisition unit with a signal indicative of airflow through the user's nose by detecting a difference in pressure between the nasal cavity and the atmosphere.

4. The system of claim 1 further comprising at least one wireless sensor in wireless communication with the data acquisition unit to provide the data acquisition unit with data indicative of a physiological state of the user during sleep, the at least one wireless sensor configured to be separate from the sensor strip.

5. The system of claim 4 wherein the data acquisition unit aligns the data collected from the at least one sensor in the sensor strip with the data provided by the at least one wireless sensor based on timestamp information.

6. The system of claim 4, further comprising at least one executable software module that determines the physiological state of the user during sleep based on changes in oxyhemoglobin saturation.

7. The system of claim 1 wherein the at least one sensor includes at least one electrode for measuring one or more of electroencephalography (EEG), electro-oculargraphy (EOG), and electromyography (EMG) and at least one reflectance sensor.

8. The system of claim 1, wherein the at least one sensor comprises at least two sensors configured to collect data of a different type.

9. The system of claim 1 wherein the sensor strip is disposable and the tab of the sensor strip can be decoupled from the data acquisition unit.

10. The system of claim 9 wherein the sensor strip includes an adhesive backing for removeably affixing the sensor strip to the user's body.

11. The system of claim 1 further comprising a microphone which detects snoring, wherein the data acquisition is in communication with the microphone to collect data indicative of snoring.

12. The system of claim 1 further comprising at least one executable software module, wherein the data acquisition unit collects data from at least two sensors, and wherein the at least one executable software module distinguishes abnormal from normal sleep states and continuity of the user based at least in part on a measure of agreement between the data collected from the at least two sensors.

13. The system of claim 12, wherein the at least one executable software module additionally identifies one or more diseases which may be negatively impacted by the user's sleep quality using a comparative data store of subjects.

14. The system of claim 13, wherein the at least one executable software module additionally identifies one or more recommendations for treatment of the identified one or more diseases using a disease recommendations data store.

15. The system of claim 12 further comprising an external computer system which receives data collected by the data acquisition unit from the data acquisition unit, wherein the at least one executable software module is executed on the external computer system.

16. The system of claim 12, wherein the at least one executable software module comprises a web portal comprising one or more user interfaces.

17. The system of claim 16, wherein the web portal provides viewing and editing of the data.

18. The system of claim 12, wherein the at least one executable software module distinguishes abnormal sleep states and continuity using patterns of sympathetic, cortical, or behavioral arousals of the user.

19. The system of claim 1, further comprising at least one executable module that:

recognizes rapid eye movement (REM) states based on ratios between electroencephalographic (EEG) beta and delta power;
recognizes slow wave sleep states based on ratios of EEG delta, beta, and theta power; and
recognizes light non-REM sleep states based on short duration fast-frequency EEG bursts indicative of sleep spindles.

20. The system of claim 1, wherein the connector comprises a socket connection.

21. The system of claim 1, wherein the at least one sensor comprises at least two sensors, and the system further comprises at least one executable software module that receives the data collected by the data acquisition unit, and determines a quality of the user's sleep based, at least in part, on the concordance of normal and abnormal patterns across the collected data.

22. The system of claim 21, wherein the at least one executable software module determines two or more potential underlying medical conditions of the user based, at least in part, on the determined quality of the user's sleep.

23. The system of claim 22, wherein the at least one executable software module further, for each of the two or more potential underlying medical conditions, determines a probability estimate that the user has or will develop the potential underlying medical condition.

24. The system of claim 22, wherein the at least one executable software module determines the two or more potential underlying medical conditions of the user further based, in part, on daytime psychophysiological states of the user.

25. The system of claim 22, wherein the at least one executable software module determines the two or more potential underlying medical conditions of the user further based, in part, on biological markers.

26. The system of claim 22, wherein the at least one executable software module further compares the determined quality of the user's sleep to a database of corresponding values.

27. The system of claim 1, wherein the data acquisition unit is configured to receive cardio-physiologic data from one or more cardio-physiologic sensors.

28. The system of claim 27, further comprising the one or more cardio-physiologic sensors, wherein the one or more cardio-physiologic sensors are separate from the sensor strip.

29. The system of claim 27, further comprising at least one executable software module that:

receives the data indicative of normal and abnormal patterns during sleep;
receives the cardio-physiologic data;
measures non-abating sympathetic hyperactivity based, at least in part, on the cardio-physiologic data; and
determines one or more potential underlying medical conditions of the user based, at least in part, on the data indicative of normal and abnormal patterns during sleep and the measure of non-abating sympathetic hyperactivity.

30. The system of claim 1, further comprising at least one executable software module that determines one or more potential underlying medical conditions of the user based on frequency characteristics of one or more sleep states of the user.

31. The system of claim 30, wherein the at least one executable software module resides in the data acquisition unit.

32. The system of claim 30, wherein the at least one executable software module resides on a computer system which is external to the data acquisition unit.

* * * * *

UNITED STATES PATENT AND TRADEMARK OFFICE
CERTIFICATE OF CORRECTION

PATENT NO.      : 8,355,769 B2
APPLICATION NO. : 12/726084
DATED           : January 15, 2013
INVENTOR(S)     : Daniel J. Levendowski et al.

It is certified that error appears in the above-identified patent and that said Letters Patent is hereby corrected as shown below:

Before the heading "RELATED APPLICATION" on Column 1, Line 4, insert as the first paragraph of the Specification:

--This invention was made with government support under Contract No. W3194Q-09-C-0281, awarded by the Defense Advanced Research Projects Agency (DARPA), under the Small Business Innovation Research (SBIR) program. The government has certain rights in the invention.--

Signed and Sealed this
Eighteenth Day of August, 2015

Michelle K. Lee
*Director of the United States Patent and Trademark Office*